US009950041B2

(12) United States Patent
Griswold et al.

(10) Patent No.: US 9,950,041 B2
(45) Date of Patent: Apr. 24, 2018

(54) THERAPEUTIC CHARGE ENGINEERED VARIANTS OF LYSOZYME AND METHODS FOR USING SAME TO TREAT INFECTIONS

(71) Applicants: Karl Edwin Griswold, Lyme, NH (US); Thomas Carr Scanlon, Lebanon, NH (US)

(72) Inventors: Karl Edwin Griswold, Lyme, NH (US); Thomas Carr Scanlon, Lebanon, NH (US)

(73) Assignees: Karl Edwin Griswold, Lyme, NH (US); Thomas Carr Scanlon, Lebanon, NH (US)

( * ) Notice: Subject to any disclaimer, the term of this patent is extended or adjusted under 35 U.S.C. 154(b) by 153 days.

(21) Appl. No.: 14/791,979

(22) Filed: Jul. 6, 2015

(65) Prior Publication Data

US 2017/0128546 A1 May 11, 2017

Related U.S. Application Data

(63) Continuation of application No. 13/144,553, filed as application No. PCT/US2010/021363 on Jan. 19, 2010, now Pat. No. 9,074,201.

(60) Provisional application No. 61/222,780, filed on Jul. 2, 2009, provisional application No. 61/145,455, filed on Jan. 16, 2009.

(51) Int. Cl.
*C07K 14/21* (2006.01)
*C12N 9/36* (2006.01)
*A61K 39/00* (2006.01)
*A61K 38/47* (2006.01)

(52) U.S. Cl.
CPC ............ *A61K 38/47* (2013.01); *C12N 9/2462* (2013.01); *C12Y 302/01017* (2013.01)

(58) Field of Classification Search
CPC ............ A61B 5/14532; A61B 5/14865; A61B 5/1495; A61B 2560/0223; A61B 5/7203; A61B 5/742; A61B 5/14542; B33Y 70/00; B33Y 80/00; C12N 9/2462; A61K 38/00; A61K 38/47; C12Q 1/006; C12Y 302/01017
See application file for complete search history.

(56) References Cited

U.S. PATENT DOCUMENTS

| | | | |
|---|---|---|---|
| 9,074,201 | B2 | 7/2015 | Griswold et al. |
| 2008/0118489 | A1 | 5/2008 | Wong et al. |

FOREIGN PATENT DOCUMENTS

| | | | |
|---|---|---|---|
| WO | 2010/083504 A2 | 7/2010 | |

OTHER PUBLICATIONS

Illustrated Stedman's Medical Dictionary. 24th Edition, Williams and Wilkins, London, p. 707, 1982.*
Dao-Pin et al. "Cumulative site-directed charge-change replacements in bacteriophage T4 lysozyme suggest that long-range electrostatic interactions contribute little to protein stability." Journal of molecular biology 221.3 (1991): 873-887.
Dong et al. "Electrostatic contributions to T4 lysozyme stability: solvent-exposed charges versus semi-buried salt bridges," Biophysical Journal. 83 (2002): 1341-1347.
Gill et al. "Crystal structure of a charge engineered human lysozyme having enhanced bactericidal activity." PloS one 6.3 (2011): e16788.
Griswold et al. "Bioengineered lysozyme in combination therapies for Pseudomonas aeruginosa lung infections." Bioengineered 5.2 (2014): 15-14.
Guaqueta et al. "The effect of salt on self-assembled actin-lysozyme complexes." Biophysical journal 90.12 (2006): 4630-4638.
Muraki et al. "A structural requirement in the subsite F of lysozyme." European Journal of Biochemistry 179.3 (1989): 573-579.
Muraki et al. "Engineering of human lysozyme as a polyelectrolyte by the alteration of molecular surface charge." Protein engineering 2.1 (1988): 49-54.
Park et al. "Influences of animal mucins on lysozyme activity in solution and on hydroxyapatite surfaces." Archives of oral biology 51.10 (2006): 861-869.
Sanders et al. "Control of electrostatic interactions between F-actin and genetically modified lysozyme in aqueous media," Proc. Natl. Acad. Sci. USA. 104.41 (2007): 15994-15999.
Sanders et al. "Structure and stability of self-assembled actin-lysozyme complexes in salty water." Physical review letters 95.10 (2005): 108302.
Scanlon et al. "Enhanced antimicrobial activity of engineered human lysozyme." ACS chemical biology 5.9 (2010): 809-818.
Tang et al. "Anionic poly(amino acid)s dissolve F-actin and DNA bundles, enhance DNase activity, and reduce the viscosity of cystic fibrosis sputum," Am. J. Physiol. Lung Cell. Mol. Physiol. 289.4 (2005): L599-L605.
Teneback et al. "Bioengineered lysozyme reduces bacterial burden and inflammation in a murine model of mucoid Pseudomonas aeruginosa lung infection." Antimicrobial agents and chemotherapy 57.11 (2013): 5559-5564.

(Continued)

*Primary Examiner* — S. Devi
(74) *Attorney, Agent, or Firm* — Lathrop Gage LLP; Brian C. Trinque

(57) ABSTRACT

The present invention is a genetically engineered version of a lysozyme protein wherein the engineered enzyme exhibits enhanced antimicrodial activity, relative to the wild type enzyme, as a result of a reduced overall electrostatic charge. Such an enzyme is an attractive therapeutic candidate for treating microbial or viral infections, particularly in cases where the infection results in an accumulation of polyanion inhibitors at the site of infection. Respiratory tract infections are one example of an infection where such an enzyme might be a particularly useful drug.

1 Claim, 7 Drawing Sheets

(56) References Cited

OTHER PUBLICATIONS

Van De Weert et al. "Complex coacervation of lysozyme and heparin: complex characterization and protein stability." Pharmaceutical research 21.12 (2004): 2354-2359.

Van Seuningen et al. "Strong ionic interactions between mucins and two basic proteins, mucus proteinase inhibitor and lysozyme, in human bronchial secretions." International Journal of Biochemistry 24.2 (1992): 303-311.

Zschornig et al. "Modulation of lysozyme charge influences interaction with phospholipid vesicles." Colloids and Surfaces B: Biointerfaces 42.1 (2005): 69-78.

International Search Report with Written Opinion corresponding to International Patent Application No. PCT/US2010/021363, dated Sep. 2, 2010.

* cited by examiner

SEQUENCE LISTING

```
<160> NUMBER OF SEQ ID NOS: 36

<210> SEQ ID NO 1
<211> LENGTH: 130
<212> TYPE: PRT
<213> ORGANISM: Artificial Sequence
<220> FEATURE:
<223> OTHER INFORMATION: Genetically engineered protein variant 2-3-7
      of human lysozyme exhibiting reduced molecular charge and
      enhanced antimicrobial activity

<400> SEQUENCE: 1

Lys Val Phe Glu Arg Cys Glu Leu Ala Arg Thr Leu Lys Arg Leu Gly
```

-continued

```
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Asp Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130


<210> SEQ ID NO 2
<211> LENGTH: 130
<212> TYPE: PRT
<213> ORGANISM: Artificial Sequence
<220> FEATURE:
<223> OTHER INFORMATION: Genetically engineered protein variant 2-1-1
      of human lysozyme exhibiting reduced molecular charge and
      enhanced antimicrobial activity

<400> SEQUENCE: 2

Lys Val Phe Glu Arg Cys Glu Leu Ala Arg Thr Leu Lys Asp Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Asp Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 3
<211> LENGTH: 130
<212> TYPE: PRT
<213> ORGANISM: Artificial Sequence
<220> FEATURE:
<223> OTHER INFORMATION: Genetically engineered protein variant 2-1-2
      of human lysozyme exhibiting reduced molecular charge and
      enhanced antimicrobial activity

<400> SEQUENCE: 3

Lys Val Phe Glu Arg Cys Glu Leu Ala Arg Thr Leu Lys Asn Leu Gly
1               5                   10                  15
```

```
Met Asp Gly Tyr Ala Gly Ile Ser Leu Ala Asn Trp Met Cys Leu Ala
            20                  25                  30

Lys Trp Glu Ser Gly Tyr Asn Thr Asp Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 4
<211> LENGTH: 130
<212> TYPE: PRT
<213> ORGANISM: Artificial Sequence
<220> FEATURE:
<223> OTHER INFORMATION: Genetically engineered protein variant 2-3-1
      of human lysozyme exhibiting reduced molecular charge and
      enhanced antimicrobial activity

<400> SEQUENCE: 4

Lys Val Phe Glu Arg Cys Glu Leu Ala Arg Thr Leu Lys Ala Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Asp Leu Ser
65                  70                  75                  80

Cys Ser Ala Leu Leu Gln Asp Asn Ile Ala Asp Ala Val Ala Cys Ala
                85                  90                  95

Lys Arg Val Val Asp Asp Pro Gln Gly Ile Arg Ala Trp Val Ala Trp
            100                 105                 110

Arg Asn Ala Cys Gln Asn Arg Asp Val Ala Gln Tyr Val Gln Gly Cys
        115                 120                 125

Gly Val
    130


<210> SEQ ID NO 5
<211> LENGTH: 130
<212> TYPE: PRT
<213> ORGANISM: Artificial Sequence
<220> FEATURE:
<223> OTHER INFORMATION: Genetically engineered protein variant 2-3-2
      of human lysozyme exhibiting reduced molecular charge and
      enhanced antimicrobial activity

<400> SEQUENCE: 5

Lys Val Phe Glu Arg Cys Glu Leu Ala Arg Thr Leu Lys Asp Leu Gly
1               5                   10                  15
```

```
Met Asp Gly Tyr Ala Gly Ile Ser Leu Ala Asn Trp Met Cys Leu Ala
            20                  25                  30

Lys Trp Glu Ser Gly Tyr Asn Thr Asp Ala Thr Asn Tyr Asn Ala Gly
        35                  40                  45

Asp Asp Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Asp Cys Gln Asn Arg Asp Val Arg Gln Tyr Val Gln Gly Cys
        115                 120                 125

Gly Val
    130


<210> SEQ ID NO 6
<211> LENGTH: 130
<212> TYPE: PRT
<213> ORGANISM: Artificial Sequence
<220> FEATURE:
<223> OTHER INFORMATION: Genetically engineered protein variant 2-3-3
      of human lysozyme exhibiting reduced molecular charge and
      enhanced antimicrobial activity

<400> SEQUENCE: 6

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Asp Asp Pro Gln Gly Ile Arg Ala Trp Val Ala Trp
            100                 105                 110

Arg Asn Ala Cys Gln Asn Arg Asp Val Arg Gln Tyr Val Gln Gly Cys
        115                 120                 125

Gly Val
    130


<210> SEQ ID NO 7
<211> LENGTH: 130
<212> TYPE: PRT
<213> ORGANISM: Artificial Sequence
<220> FEATURE:
<223> OTHER INFORMATION: Genetically engineered protein variant 2-3-4
      of human lysozyme exhibiting reduced molecular charge and
      enhanced antimicrobial activity

<400> SEQUENCE: 7

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
```

```
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Asp Leu Ser
65                  70                  75                  80

Cys Ser Ala Leu Leu Gln Asp Asn Ile Ala Asp Ala Val Ala Cys Ala
                85                  90                  95

Lys Arg Val Val Ala Asp Pro Gln Gly Ile Arg Ala Trp Val Ala Trp
            100                 105                 110

Arg Asn Asn Cys Gln Asn Arg Asp Val Arg Gln Tyr Val Gln Gly Cys
        115                 120                 125

Gly Val
    130


<210> SEQ ID NO 8
<211> LENGTH: 130
<212> TYPE: PRT
<213> ORGANISM: Artificial Sequence
<220> FEATURE:
<223> OTHER INFORMATION: Genetically engineered protein variant 2-3-5
      of human lysozyme exhibiting reduced molecular charge and
      enhanced antimicrobial activity

<400> SEQUENCE: 8

Lys Val Phe Glu Arg Cys Glu Leu Ala Arg Thr Leu Lys Ala Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Asp Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 9
<211> LENGTH: 130
<212> TYPE: PRT
<213> ORGANISM: Artificial Sequence
<220> FEATURE:
<223> OTHER INFORMATION: Genetically engineered protein variant 2-3-8
      of human lysozyme exhibiting reduced molecular charge and
      enhanced antimicrobial activity

<400> SEQUENCE: 9

Lys Val Phe Glu Arg Cys Glu Leu Ala Arg Thr Leu Lys Asn Leu Gly
1               5                   10                  15

Met Asp Gly Tyr Ala Gly Ile Ser Leu Ala Asn Trp Met Cys Leu Ala
            20                  25                  30
```

```
Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Asp Asp Pro Gln Gly Ile Arg Ala Trp Val Ala Trp
            100                 105                 110

Arg Asn Arg Cys Gln Asn Arg Asp Val Ala Gln Tyr Val Gln Gly Cys
        115                 120                 125

Gly Val
    130


<210> SEQ ID NO 10
<211> LENGTH: 130
<212> TYPE: PRT
<213> ORGANISM: Artificial Sequence
<220> FEATURE:
<223> OTHER INFORMATION: Genetically engineered protein variant 2-3-9
      of human lysozyme exhibiting reduced molecular charge and
      enhanced antimicrobial activity

<400> SEQUENCE: 10

Lys Val Phe Glu Arg Cys Glu Leu Ala Arg Thr Leu Lys Ala Leu Gly
1               5                   10                  15

Met Asp Gly Tyr Asn Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Asp Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Asn Leu Ser
65                  70                  75                  80

Cys Ser Ala Leu Leu Gln Asp Asn Ile Ala Asp Ala Val Ala Cys Ala
                85                  90                  95

Lys Arg Val Val Asp Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 11
<211> LENGTH: 130
<212> TYPE: PRT
<213> ORGANISM: Artificial Sequence
<220> FEATURE:
<223> OTHER INFORMATION: Genetically engineered protein variant 2-3-10
      of human lysozyme exhibiting reduced molecular charge and
      enhanced antimicrobial activity

<400> SEQUENCE: 11

Lys Val Phe Glu Arg Cys Glu Leu Ala Arg Thr Leu Lys Ala Leu Gly
1               5                   10                  15

Met Asp Gly Tyr Ala Gly Ile Ser Leu Ala Asn Trp Met Cys Leu Ala
            20                  25                  30
```

```
Lys Trp Glu Ser Gly Tyr Asn Thr Arg Ala Thr Asn Tyr Asn Ala Gly
        35                  40                  45

Asp Ala Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 12
<211> LENGTH: 130
<212> TYPE: PRT
<213> ORGANISM: Artificial Sequence
<220> FEATURE:
<223> OTHER INFORMATION: Genetically engineered protein variant 2-3-11
      of human lysozyme exhibiting reduced molecular charge and
      enhanced antimicrobial activity

<400> SEQUENCE: 12

Lys Val Phe Glu Arg Cys Glu Leu Ala Arg Thr Leu Lys Ala Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Ala Leu Ser
65                  70                  75                  80

Cys Ser Ala Leu Leu Gln Asp Asn Ile Ala Asp Ala Val Ala Cys Ala
                85                  90                  95

Lys Arg Val Val Ala Asp Pro Gln Gly Ile Arg Ala Trp Val Ala Trp
            100                 105                 110

Arg Asn Arg Cys Gln Asn Arg Asp Val Asp Gln Tyr Val Gln Gly Cys
        115                 120                 125

Gly Val
    130


<210> SEQ ID NO 13
<211> LENGTH: 130
<212> TYPE: PRT
<213> ORGANISM: Artificial Sequence
<220> FEATURE:
<223> OTHER INFORMATION: Genetically engineered protein variant 2-3-12
      of human lysozyme exhibiting reduced molecular charge and
      enhanced antimicrobial activity

<400> SEQUENCE: 13

Lys Val Phe Glu Arg Cys Glu Leu Ala Arg Thr Leu Lys Asn Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
```

35 40 45

Asp Arg Ser Thr Asp Tyr Gly Ile Phe Gln Ile Asn Ser Arg Tyr Trp
50 55 60

Cys Asn Asp Gly Lys Thr Pro Gly Ala Val Asn Ala Cys Asp Leu Ser
65 70 75 80

Cys Ser Ala Leu Leu Gln Asp Asn Ile Ala Asp Ala Val Ala Cys Ala
85 90 95

Lys Arg Val Val Arg Asp Pro Gln Gly Ile Arg Ala Trp Val Ala Trp
100 105 110

Arg Asn Asn Cys Gln Asn Arg Asp Val Arg Gln Tyr Val Gln Gly Cys
115 120 125

Gly Val
130

<210> SEQ ID NO 14
<211> LENGTH: 130
<212> TYPE: PRT
<213> ORGANISM: Artificial Sequence
<220> FEATURE:
<223> OTHER INFORMATION: Genetically engineered protein variant 2-5-1 of human lysozyme exhibiting reduced molecular charge and enhanced antimicrobial activity

<400> SEQUENCE: 14

Lys Val Phe Glu Arg Cys Glu Leu Ala Arg Thr Leu Lys Ala Leu Gly
1 5 10 15

Met Asp Gly Tyr Asn Gly Ile Ser Leu Ala Asn Trp Met Cys Leu Ala
20 25 30

Lys Trp Glu Ser Gly Tyr Asn Thr Arg Ala Thr Asn Tyr Asn Ala Gly
35 40 45

Asp Arg Ser Thr Asp Tyr Gly Ile Phe Gln Ile Asn Ser Arg Tyr Trp
50 55 60

Cys Asn Asp Gly Lys Thr Pro Gly Ala Val Asn Ala Cys Ala Leu Ser
65 70 75 80

Cys Ser Ala Leu Leu Gln Asp Asn Ile Ala Asp Ala Val Ala Cys Ala
85 90 95

Lys Arg Val Val Arg Asp Pro Gln Gly Ile Arg Ala Trp Val Ala Trp
100 105 110

Arg Asn Arg Cys Gln Asn Arg Asp Val Arg Gln Tyr Val Gln Gly Cys
115 120 125

Gly Val
130

<210> SEQ ID NO 15
<211> LENGTH: 130
<212> TYPE: PRT
<213> ORGANISM: Artificial Sequence
<220> FEATURE:
<223> OTHER INFORMATION: Genetically engineered protein variant D9 of human lysozyme exhibiting reduced molecular charge and enhanced antimicrobial activity

<400> SEQUENCE: 15

Lys Val Phe Glu Arg Cys Glu Leu Ala Arg Thr Leu Lys Arg Leu Gly
1 5 10 15

Met Asp Gly Tyr Arg Gly Ile Ser Leu Ala Asn Trp Met Cys Leu Ala
20 25 30

Lys Trp Glu Ser Gly Tyr Asn Thr Gln Ala Thr Asn Tyr Asn Ala Gly
35 40 45

```
Asp Gln Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Gln Cys Gln Asn Arg Asp Val Arg Gln Tyr Val Gln Gly Cys
        115                 120                 125

Gly Val
    130


<210> SEQ ID NO 16
<211> LENGTH: 130
<212> TYPE: PRT
<213> ORGANISM: Artificial Sequence
<220> FEATURE:
<223> OTHER INFORMATION: Genetically engineered protein variant E4
      of human lysozyme exhibiting reduced molecular charge and
      enhanced antimicrobial activity

<400> SEQUENCE: 16

Lys Val Phe Glu Arg Cys Glu Leu Ala Arg Thr Leu Lys Glu Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Gln Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 17
<211> LENGTH: 130
<212> TYPE: PRT
<213> ORGANISM: Artificial Sequence
<220> FEATURE:
<223> OTHER INFORMATION: Genetically engineered protein variant F10
      of human lysozyme exhibiting reduced molecular charge and
      enhanced antimicrobial activity

<400> SEQUENCE: 17

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45
```

```
Asp Ala Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Gln Cys Gln Asn Arg Asp Val Arg Gln Tyr Val Gln Gly Cys
        115                 120                 125

Gly Val
    130


<210> SEQ ID NO 18
<211> LENGTH: 130
<212> TYPE: PRT
<213> ORGANISM: Artificial Sequence
<220> FEATURE:
<223> OTHER INFORMATION: Genetically engineered protein variant G6
      of human lysozyme exhibiting reduced molecular charge and
      enhanced antimicrobial activity

<400> SEQUENCE: 18

Lys Val Phe Glu Arg Cys Glu Leu Ala Arg Thr Leu Lys Ala Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Gln Cys Gln Asn Arg Asp Val Arg Gln Tyr Val Gln Gly Cys
        115                 120                 125

Gly Val
    130


<210> SEQ ID NO 19
<211> LENGTH: 130
<212> TYPE: PRT
<213> ORGANISM: Artificial Sequence
<220> FEATURE:
<223> OTHER INFORMATION: Genetically engineered protein variant D7
      of human lysozyme exhibiting reduced molecular charge and
      enhanced antimicrobial activity

<400> SEQUENCE: 19

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
```

```
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Ala Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 20
<211> LENGTH: 130
<212> TYPE: PRT
<213> ORGANISM: Artificial Sequence
<220> FEATURE:
<223> OTHER INFORMATION: Genetically engineered protein variant F8
      of human lysozyme exhibiting reduced molecular charge and
      enhanced antimicrobial activity

<400> SEQUENCE: 20

Lys Val Phe Glu Arg Cys Glu Leu Ala Arg Thr Leu Lys Glu Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 21
<211> LENGTH: 130
<212> TYPE: PRT
<213> ORGANISM: Artificial Sequence
<220> FEATURE:
<223> OTHER INFORMATION: Genetically engineered protein variant G4
      of human lysozyme exhibiting reduced molecular charge and
      enhanced antimicrobial activity

<400> SEQUENCE: 21

Lys Val Phe Glu Arg Cys Glu Leu Ala Arg Thr Leu Lys Ala Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Glu Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60
```

```
Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 22
<211> LENGTH: 130
<212> TYPE: PRT
<213> ORGANISM: Artificial Sequence
<220> FEATURE:
<223> OTHER INFORMATION: Genetically engineered protein variant A3
      of human lysozyme exhibiting reduced molecular charge and
      enhanced antimicrobial activity

<400> SEQUENCE: 22

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Ala Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Ala Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 23
<211> LENGTH: 130
<212> TYPE: PRT
<213> ORGANISM: Artificial Sequence
<220> FEATURE:
<223> OTHER INFORMATION: Genetically engineered protein variant B3
      of human lysozyme exhibiting reduced molecular charge and
      enhanced antimicrobial activity

<400> SEQUENCE: 23

Lys Val Phe Glu Arg Cys Glu Leu Ala Arg Thr Leu Lys Gln Leu Gly
1               5                   10                  15

Met Asp Gly Tyr Gln Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Ala Ser Thr Asp Tyr Gly Ile Phe Gln Ile Asn Ser Arg Tyr Trp
    50                  55                  60
```

Cys Asn Asp Gly Lys Thr Pro Gly Ala Val Asn Ala Cys Ala Leu Ser
65 70 75 80

Cys Ser Ala Leu Leu Gln Asp Asn Ile Ala Asp Ala Val Ala Cys Ala
85 90 95

Lys Arg Val Val Arg Asp Pro Gln Gly Ile Arg Ala Trp Val Ala Trp
100 105 110

Arg Asn Arg Cys Gln Asn Arg Asp Val Arg Gln Tyr Val Gln Gly Cys
115 120 125

Gly Val
130

<210> SEQ ID NO 24
<211> LENGTH: 130
<212> TYPE: PRT
<213> ORGANISM: Artificial Sequence
<220> FEATURE:
<223> OTHER INFORMATION: Genetically engineered protein variant B4 of human lysozyme exhibiting reduced molecular charge and enhanced antimicrobial activity

<400> SEQUENCE: 24

Lys Val Phe Glu Arg Cys Glu Leu Ala Arg Thr Leu Lys Gln Leu Gly
1 5 10 15

Met Asp Gly Tyr Ala Gly Ile Ser Leu Ala Asn Trp Met Cys Leu Ala
20 25 30

Lys Trp Glu Ser Gly Tyr Asn Thr Arg Ala Thr Asn Tyr Asn Ala Gly
35 40 45

Asp Glu Ser Thr Asp Tyr Gly Ile Phe Gln Ile Asn Ser Arg Tyr Trp
50 55 60

Cys Asn Asp Gly Lys Thr Pro Gly Ala Val Asn Ala Cys His Leu Ser
65 70 75 80

Cys Ser Ala Leu Leu Gln Asp Asn Ile Ala Asp Ala Val Ala Cys Ala
85 90 95

Lys Arg Val Val Gln Asp Pro Gln Gly Ile Arg Ala Trp Val Ala Trp
100 105 110

Arg Asn Arg Cys Gln Asn Arg Asp Val Arg Gln Tyr Val Gln Gly Cys
115 120 125

Gly Val
130

<210> SEQ ID NO 25
<211> LENGTH: 130
<212> TYPE: PRT
<213> ORGANISM: Artificial Sequence
<220> FEATURE:
<223> OTHER INFORMATION: Genetically engineered protein variant C3 of human lysozyme exhibiting reduced molecular charge and enhanced antimicrobial activity

<400> SEQUENCE: 25

Lys Val Phe Glu Arg Cys Glu Leu Ala Arg Thr Leu Lys Ala Leu Gly
1 5 10 15

Met Asp Gly Tyr Gln Gly Ile Ser Leu Ala Asn Trp Met Cys Leu Ala
20 25 30

Lys Trp Glu Ser Gly Tyr Asn Thr Gln Ala Thr Asn Tyr Asn Ala Gly
35 40 45

Asp Arg Ser Thr Asp Tyr Gly Ile Phe Gln Ile Asn Ser Arg Tyr Trp
50 55 60

Cys Asn Asp Gly Lys Thr Pro Gly Ala Val Asn Ala Cys Ala Leu Ser

```
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 26
<211> LENGTH: 130
<212> TYPE: PRT
<213> ORGANISM: Artificial Sequence
<220> FEATURE:
<223> OTHER INFORMATION: Genetically engineered protein variant C6
      of human lysozyme exhibiting reduced molecular charge and
      enhanced antimicrobial activity

<400> SEQUENCE: 26

Lys Val Phe Glu Arg Cys Glu Leu Ala Arg Thr Leu Lys Arg Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Gln Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Ala Leu Ser
65                  70                  75                  80

Cys Ser Ala Leu Leu Gln Asp Asn Ile Ala Asp Ala Val Ala Cys Ala
                85                  90                  95

Lys Arg Val Val Gln Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 27
<211> LENGTH: 130
<212> TYPE: PRT
<213> ORGANISM: Artificial Sequence
<220> FEATURE:
<223> OTHER INFORMATION: Genetically engineered protein variant D6
      of human lysozyme exhibiting reduced molecular charge and
      enhanced antimicrobial activity

<400> SEQUENCE: 27

Lys Val Phe Glu Arg Cys Glu Leu Ala Arg Thr Leu Lys Glu Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80
```

```
Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 28
<211> LENGTH: 130
<212> TYPE: PRT
<213> ORGANISM: Artificial Sequence
<220> FEATURE:
<223> OTHER INFORMATION: Genetically engineered protein variant F9
      of human lysozyme exhibiting reduced molecular charge and
      enhanced antimicrobial activity

<400> SEQUENCE: 28

Lys Val Phe Glu Arg Cys Glu Leu Ala Arg Thr Leu Lys Gln Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Gln Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Glu Leu Ser
65                  70                  75                  80

Cys Ser Ala Leu Leu Gln Asp Asn Ile Ala Asp Ala Val Ala Cys Ala
                85                  90                  95

Lys Arg Val Val Glu Asp Pro Gln Gly Ile Arg Ala Trp Val Ala Trp
            100                 105                 110

Arg Asn Arg Cys Gln Asn Arg Asp Val Arg Gln Tyr Val Gln Gly Cys
        115                 120                 125

Gly Val
    130


<210> SEQ ID NO 29
<211> LENGTH: 130
<212> TYPE: PRT
<213> ORGANISM: Artificial Sequence
<220> FEATURE:
<223> OTHER INFORMATION: Genetically engineered protein variant A111
      of human lysozyme exhibiting reduced molecular charge and
      enhanced antimicrobial activity

<400> SEQUENCE: 29

Lys Val Phe Glu Arg Cys Glu Leu Ala Arg Thr Leu Lys Ala Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Glu Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80
```

```
Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130


<210> SEQ ID NO 30
<211> LENGTH: 130
<212> TYPE: PRT
<213> ORGANISM: Artificial Sequence
<220> FEATURE:
<223> OTHER INFORMATION: Genetically engineered protein variant C13
      of human lysozyme exhibiting reduced molecular charge and
      enhanced antimicrobial activity

<400> SEQUENCE: 30

Lys Val Phe Glu Arg Cys Glu Leu Ala Arg Thr Leu Lys Glu Leu Gly
1               5                   10                  15

Met Asp Gly Tyr Gln Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130


<210> SEQ ID NO 31
<211> LENGTH: 130
<212> TYPE: PRT
<213> ORGANISM: Artificial Sequence
<220> FEATURE:
<223> OTHER INFORMATION: Genetically engineered protein variant G15
      of human lysozyme exhibiting reduced molecular charge and
      enhanced antimicrobial activity

<400> SEQUENCE: 31

Lys Val Phe Glu Arg Cys Glu Leu Ala Arg Thr Leu Lys Asn Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
```

```
                85                  90                  95

Lys Arg Val Val Arg Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130


<210> SEQ ID NO 32
<211> LENGTH: 130
<212> TYPE: PRT
<213> ORGANISM: Artificial Sequence
<220> FEATURE:
<223> OTHER INFORMATION: Genetically engineered protein variant G18
      of human lysozyme exhibiting reduced molecular charge and
      enhanced antimicrobial activity

<400> SEQUENCE: 32

Lys Val Phe Glu Arg Cys Glu Leu Ala Arg Thr Leu Lys Ala Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130


<210> SEQ ID NO 33
<211> LENGTH: 130
<212> TYPE: PRT
<213> ORGANISM: Artificial Sequence
<220> FEATURE:
<223> OTHER INFORMATION: Genetically engineered protein variant A26
      of human lysozyme exhibiting reduced molecular charge and
      enhanced antimicrobial activity

<400> SEQUENCE: 33

Lys Val Phe Glu Arg Cys Glu Leu Ala Arg Thr Leu Lys Ala Leu Gly
1               5                   10                  15

Met Asp Gly Tyr Gln Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95
```

```
Lys Arg Val Val Arg Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130


<210> SEQ ID NO 34
<211> LENGTH: 130
<212> TYPE: PRT
<213> ORGANISM: Artificial Sequence
<220> FEATURE:
<223> OTHER INFORMATION: Genetically engineered protein variant G211
      of human lysozyme exhibiting reduced molecular charge and
      enhanced antimicrobial activity

<400> SEQUENCE: 34

Lys Val Phe Glu Arg Cys Glu Leu Ala Arg Thr Leu Lys Ala Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Gln Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Ala Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130


<210> SEQ ID NO 35
<211> LENGTH: 130
<212> TYPE: PRT
<213> ORGANISM: Artificial Sequence
<220> FEATURE:
<223> OTHER INFORMATION: Genetically engineered protein variant C25
      of human lysozyme exhibiting reduced molecular charge and
      enhanced antimicrobial activity

<400> SEQUENCE: 35

Lys Val Phe Glu Arg Cys Glu Leu Ala Arg Thr Leu Lys Glu Leu Gly
1               5                   10                  15

Met Asp Gly Tyr Arg Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Arg Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys His Leu Ser
65                  70                  75                  80

Cys Ser Ala Leu Leu Gln Asp Asn Ile Ala Asp Ala Val Ala Cys Ala
                85                  90                  95
```

-continued

```
Lys Arg Val Val Ala Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130


<210> SEQ ID NO 36
<211> LENGTH: 130
<212> TYPE: PRT
<213> ORGANISM: Artificial Sequence
<220> FEATURE:
<223> OTHER INFORMATION: Genetically engineered protein variant D25
      of human lysozyme exhibiting reduced molecular charge and
      enhanced antimicrobial activity

<400> SEQUENCE: 36

Lys Val Phe Glu Arg Cys Glu Leu Ala Arg Thr Leu Lys Ala Leu Gly
1               5                   10                  15

Met Asp Gly Tyr Ala Gly Ile Ser Leu Ala Asn Trp Met Cys Leu Ala
            20                  25                  30

Lys Trp Glu Ser Gly Tyr Asn Thr Arg Ala Thr Asn Tyr Asn Ala Gly
        35                  40                  45

Asp Ala Ser Thr Asp Tyr Gly Ile Phe Gln Ile Asn Ser Arg Tyr Trp
    50                  55                  60

Cys Asn Asp Gly Lys Thr Pro Gly Ala Val Asn Ala Cys Gln Leu Ser
65                  70                  75                  80

Cys Ser Ala Leu Leu Gln Asp Asn Ile Ala Asp Ala Val Ala Cys Ala
                85                  90                  95

Lys Arg Val Val Arg Asp Pro Gln Gly Ile Arg Ala Trp Val Ala Trp
            100                 105                 110

Arg Asn His Cys Gln Asn Arg Asp Val Arg Gln Tyr Val Gln Gly Cys
        115                 120                 125

Gly Val
    130
```

THERAPEUTIC CHARGE ENGINEERED VARIANTS OF LYSOZYME AND METHODS FOR USING SAME TO TREAT INFECTIONS

RELATED APPLICATIONS

This application is a continuation of U.S. application Ser. No. 13/144,553, filed Oct. 3, 2011, now U.S. Pat. No. 9,074,201, which is a 371 national stage entry of international application number PCT/US2010/21363, filed Jan. 19, 2010, which claims priority to U.S. Provisional Application No. 61/145,455, filed Jan. 16, 2009, titled "THERAPEUTIC CHARGE ENGINEERED VARIANTS OF LYSOZYME AND METHODS FOR USING THE SAME TO TREAT INFECTIONS" and also claims priority to U.S. Provisional Application No. 61/222,780, filed Jul. 2, 2009, titled "THERAPEUTIC CHARGE ENGINEERED VARIANTS OF LYSOZYME AND METHODS FOR USING THE SAME TO TREAT INFECTIONS." The contents of any patents, patent applications, and references cited throughout this specification are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, created on Sep. 21, 2015, is named 571505.txt and is 53,248 bytes in size.

BACKGROUND OF THE INVENTION

It is infrequently recognized that lung infections are the leading cause of combined morbidity and mortality worldwide (1). A diverse array of microbes and viruses are responsible for causing lower respiratory tract infections % Pathogenic bacteria account for a large proportion of these diseases including community acquired pneumonia, hospital acquired pneumonia, and ventilator associated pneumonia, which together affect more than 4 million people in the United States annually (2, 3). Globally, tuberculosis continues to be a devastating disease killing more than 1.7 million people in 2004, according to the World Health Organization, in addition to being causative agents, bacterial infections of the lung are closely associated with morbidity and mortality in numerous diseases of nonbacterial origins. Examples include chronic obstructive pulmonary disease, bronchiectasis, diffuse panbronchiolitis, cystic fibrosis, and acute respiratory distress syndrome. Combined, these bacterial pulmonary infections represent a significant threat to US and global human health.

Analysis of disability-adjusted life years (a combined measure of morbidity and mortality) has revealed that the global disease burden caused by lung infections decreased little if any from 1990 to 2002, even in the world's wealthiest nations (1). Analysis of annual United States deaths from lung infections indicates that mortality rates have not improved since prior to 1950 (4). In fact, deaths from pneumonia and influenza increased by more than 50% from 1980 to 1996, While the lack of progress in treating lung infections is a complex issue dependent on numerous variables, one key element of this medical stigma is the emergence of bacterial resistance to antibiotics (5). The natural products and synthetic derivatives that have been mainstays of antimicrobial therapy (i.e. agents with selective toxicity for gram-positive bacteria, gram-negative bacteria, and/or fungi) for more than 60 years are becoming more and more ineffectual, as their ribosomal and enzyme targets accumulate adaptive mutations and resistance elements spread by horizontal gene transfer, both driven by the selective pressure of wide spread antibiotic use. The imperative for the medical and pharmaceutical communities to develop new antimicrobial agents is clear.

Accordingly, there remains a need for treatments for microbial and viral infections, such as respiratory infections.

SUMMARY OF THE INVENTION

The present invention is a genetically engineered version of a lysozyme protein (hereafter referred to as a variant) wherein the variant exhibits enhanced antimicrobial activity, relative to the wild type enzyme, as a result of a reduced overall electrostatic charge. Of particular interest are charge engineered lysozymes that exhibit enhanced antimicrobial activity in the presence of various inhibitory anionic biopolymers common in the infected lung, e.g. DNA, mucin, alginate, heparin, F-actin. Of further interest is the use of these charge engineered lysozymes as therapeutic agents for treatment of various bacterial, fungal or viral infections, especially of the respiratory tract. The engineered enzymes are isolated from large combinatorial libraries using customized plate based functional screens. The invention relates to engineered variants of any native lysozyme protein, such as variants of human lysozyme, which should exhibit a lower inherent immunogenicity in human patients than variants of non-human lysozyme homologs.

Thus, in one aspect, provided herein is a lysozyme protein having a reduced electrostatic charge, relative to the wild type protein, wherein the charge reduction is a result of mutating the wild type protein's lysine, arginine, or histidine residues to uncharged or negatively charged amino acids.

In one embodiment, the lysozyme protein is genetically engineered. In another embodiment, the lysozyme is charge reduced by chemical means, such as by attachment to negatively charged nanoparticles, or succinylation of amino groups.

In another embodiment, the protein exhibits enhanced, therapeutic antimicrobial and/or antiviral activity, relative to the wild type protein.

In yet another embodiment, the enzyme is derived from human lysozyme. In one preferred embodiment, the charge reduction of the human lysozyme protein results from mutation of arginines 14, 21, 41, 50, 101, 115, 119, 122, and/or Histidine 78 (numbered from lysine 1 of processed, mature human lysozyme). In another preferred embodiment, the enzyme's native residues are replaced with glutamic acid, aspartic acid, glutamine, asparagine, alanine, or histidine.

In another embodiment, the enzyme exhibits enhanced antimicrobial activity in the presence of alginate. In one embodiment, the enzyme has at least 3-fold increased IC50 for alginate.

In one embodiment, the lysozyme protein exhibits enhanced antimicrobial activity in the presence of DNA. In one embodiment, the enzyme has at least 43-fold increased IC50 for DNA In another embodiment, the lysozyme enzyme exhibits enhanced antimicrobial activity in the presence of mucin. In one embodiment, the enzyme has at least 6-fold increased IC50 for mucin.

In one embodiment, the lysozyme exhibits enhanced antimicrobial activity in the presence of F-actin.

In another embodiment, the lysozyme exhibits enhanced antimicrobial activity in the presence of heparin.

In still another embodiment, the lysozyme exhibits reduced affinity for bacterial cells, resulting in enhanced kinetics of bacterial killing and a consequent increase in antibacterial activity.

In another embodiment, the lysozyme is selected from the group consisting of a mammalian lysozyme, a bacterial lysozyme, a viral lysozyme, a fungal lysozyme, a reptilian lysozyme, or an avian lysozyme.

In another aspect, provided herein is a protein having a reduced electrostatic charge, relative to the wild type protein. In one embodiment, the lysozyme proteins are genetically engineered. In one preferred embodiment, the lysozyme proteins exhibit enhanced, therapeutic antimicrobial and/or antiviral activity, relative to the wild type protein.

In another aspect, provided herein is a method for treating a microbial or viral infection comprising administering to a subject having or at risk of having a microbial or viral infection an effective amount of the antimicrobial agent of any one of the above claims, such that the microbial or viral infection is treated.

In one embodiment, the microbial or viral infection is a viral infection.

In another embodiment, the microbial or viral infection is a respiratory infection.

In yet another embodiment, the method of treatment results in a reduction of the subject's microbial or viral burden.

In still another embodiment, the method of treatment results in a reduction of the inflammatory response at the site of infection.

In another embodiment, the subject has or is at risk of having a respiratory infection.

In another aspect, provided herein is the use of the lysozyme protein described herein for the manufacture of a medicament for a microbial or viral infection in a subject.

In still another embodiment, the modified lysozyme is an enzyme.

DETAILED DESCRIPTION OF THE INVENTION

Figure 1:
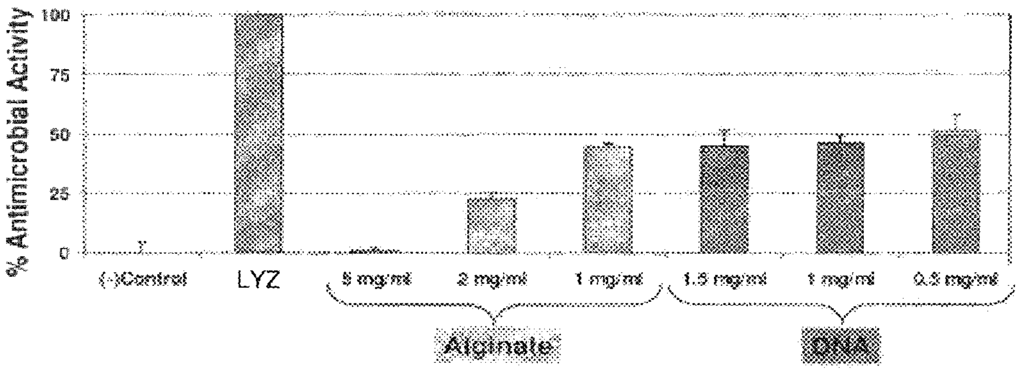
FIG. 1 shows the inhibition of wild type lysozyme activity by alginate and DNA, Activity was evaluated by measuring light scattering of *Micrococcus luteus* at 450 nm following a 15 minute incubation with 500 ng of wild type lysozyme in 200 μl of 100 mM sodium phosphate buffer pH 6.0. Measurements obtained with no lysozyme and no polyanion inhibitors were taken as zero activity; measurements with lysozyme but no polyanion inhibitors were set to 100% activity; measurements with both lysozyme and polyanion inhibitors were normalized with respect to the 100% activity measurements. Note that both polyanion inhibitors result in a loss of 50% or more activity at all tested concentrations, and that 0.5% wt/vol alginate completely abrogates all lytic activity of wild type lysozyme.

As noted, the problem of how best to treat pathogenic bacterial infections is complicated by microbial evolutionary plasticity and the resulting capacity of microorganisms to rapidly subvert virtually all enzyme inhibitors. The innate immune systems of many organisms have answered this challenge in part by devising biocidal agents that target microbial components with far less adaptability than genetically encoded proteins. Examples of these more robust antibiotics include lactoferrin (an iron chelator) and numerous cationic antimicrobial peptides that disrupt bacterial lipid membranes, Another prime example is the biocatalyst lysozyme, which degrades the peptidoglycan structural component of bacterial cell walls resulting in microbe lysis and death. Lysozyme exhibits broad spectrum antibacterial activity, and has been shown to be the most abundant (up to 1 mg/ml) and effective bactericidal agent in human airway fluids (6-8). Numerous studies have articulated lysozyme's effectiveness against both gram positive and gram negative organisms (6, 8), although its exact mechanism of action is not well understood in some cases (9). While the in vitro antimicrobial activity of lysozyme has been studied extensively for more than 80 years, the critical role of lysozyme in protecting animal airways from bacterial pathogens has only recently been experimentally verified (10-12).

While lysozyme is a highly effective antimicrobial agent under conditions near stasis, the wild type protein suffers from particular limitations under conditions typical of acute and chronic pulmonary tract infections. As a result, wild type human lysozyme is not a viable therapeutic option for treatment of many microbial lung infections. In humans, detection of invading microbes by alveolar macrophages or airway epithelial cells initiates a complex signaling pathway. The end result is the production of proinflammatory molecules at the site of infection and the subsequent chemotaxis of neutrophils (white blood cells) into the air space of the lung. Neutrophils are the elite killers of the innate cellular immune response. The mechanisms and molecular weaponry employed by neutrophils are complex and diverse. In addition to phagocytic action, they are known to release proteases, reactive oxygen species and other antimicrobial molecules (including lysozyme) into the extracellular space. This is accomplished through various mechanisms including degranulation, holocrine secretion, and controlled cell death leading to the formation of neutrophil extracellular traps (NETS) (7). While the release of these biocides is intended to kill the invading pathogens, there is invariably a considerable amount of collateral damage including lysis of the host's own airway epithelial cells. The result is a highly inflamed lung environment, a hallmark of both acute and chronic lower respiratory tract infections (13, 14).

It is known that the inflammatory response is a necessary element in the immune system's attack on bacterial pathogens, but the resulting wide spread tissue damage and coordinated self-lysis of neutrophils leads to a build up of the host's own intracellular components in the lung space. Of particular relevance is the accumulation of anionic biopolymers such as F-actin and chromosomal DNA, which can reach concentrations as high as 5 and 2.0 mg/ml in the infected lung, respectively (15). Mucin, a primary component of the mucus layer lining the airway lumen, is another highly anionic biopolymer endogenous to the lung environment. Mucin concentrations are approximately 2 mg/ml in healthy individuals, but minutes after detection of any foreign invader in the respiratory tract their levels rise dramatically (16). Evidence is also beginning to accumulate that the highly negatively charged polymer heparin plays a key role in protecting the lung from microbial or viral infection (17). A fifth anionic biopolymer found in some lung environments is the exopolysaccharide alginate, the primary component of mucoid *Pseudomonas aeruginosa* biofilms (18). It is also worth noting that in addition to the high concentration of the host's own DNA in the inflamed lung, some bacteria are known to independently secrete DNA during biofilm formation (19). Combined, these anionic biopolymers can exert a considerable effect on the electrostatic environment of the infected lung.

Increased polyanion concentrations in the infected lung have a detrimental impact on lysozyme activity resulting from sequestration of the highly cationic enzyme via coulombic effects. The isoelectric point of wild type human lysozyme is 10.5, and its charge at physiological pH is greater than +7. Therefore, it is not surprising that lysozymes are known to complex with F-actin (20), are inhibited by mucins (21), unfold and aggregate with heparin (22), and aggregate and undergo inactivation in the presence of physiologically relevant concentrations of anionic biopolymers (FIG. 1, as well as other data not shown). The inhibition of wild type human lysozyme by elements specific to the site of bacterial infection negates its therapeutic potential, particularly respiratory infections.

Complex formation between lysozyme and biological polyanions is driven by charge-charge electrostatic effects, as evidenced by studies with rationally designed charge mutants of T4 phage lysozyme (23). This indicates that remodeling human lysozyme's electrostatic potential could prevent inactivation by disrupting coulombic attractions to anionic biopolymers present in the infected lung. However, charge variants of lysozyme would have to retain high level antimicrobial activity to be considered as therapeutic options, and such a lysozyme variant has not been previously demonstrated. A human lysozyme successfully modified in this manner could represent a highly potent antimicrobial therapeutic agent useful for treating acute and chronic lung infections. As a result of the enzyme's finely tuned structure-function relationships, the ability to reduce the charge of lysozyme while maintaining its antimicrobial potency represents an unexpected outcome.

Several studies have examined how changes in the molecular charge of various lysozymes affect properties such as sweetness to taste (24), actin complex formation (23), binding to hydroxyapatite (25), and lytic activity as a function of pH and salt concentration (26-28). Using rational protein design (i.e., site-directed mutagenesis of specific protein residues), these studies have provided insights into the role played by electrostatics in various lysozyme properties. However, these experiments have invariably failed to directly address the clinically relevant issue outlined above, i.e. inhibition of lysozyme's antimicrobial activity by polyanionic, species endogenous to the inflamed lung. As a result, charge modified lysozymes revealed in the prior art have not been shown to exhibit enhanced antimicrobial or therapeutic activity (relative to the wild type protein) in the presence of polyanionic inhibitors. Previously, no group has been able to directly engage this molecular design problem, likely due to the highly coupled nature of lysozyme's positive charge and its antimicrobial activity. As implemented in these prior studies, rational protein design has the capacity to accomplish relatively straightforward objectives such as modification of a single, easily controlled property, such as electrostatic potential. However, because of the finely tuned nature of protein structure-function relationships, it has historically been an intractable task to reduce lysozyme's charge while maintaining or improving upon the wild type enzymes antimicrobial activity.

Figure 2A:
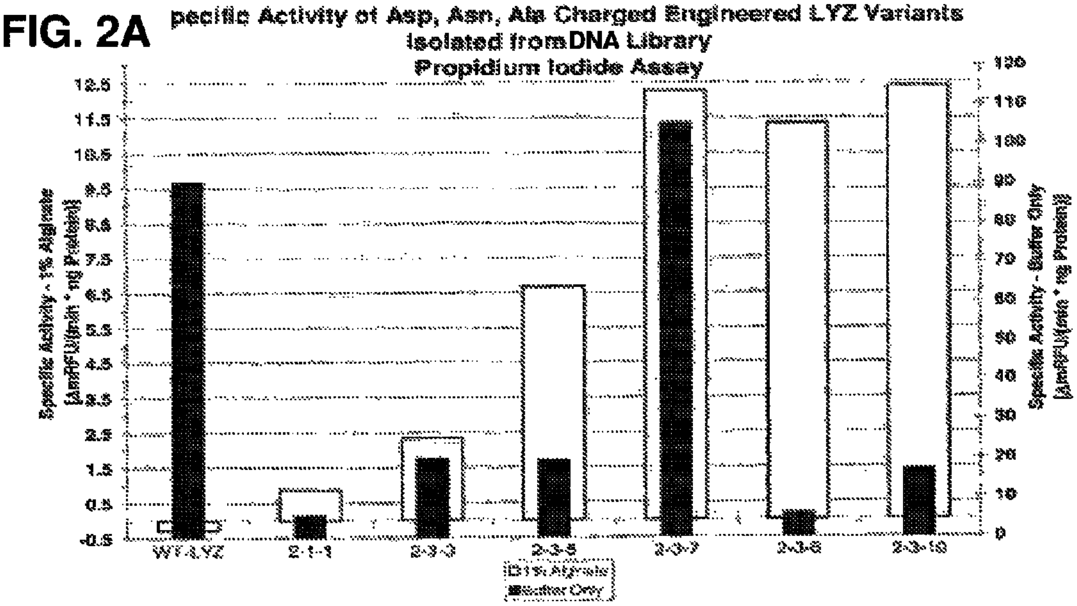
FIG. 2A and FIG. 2B show the results of fluorescence based lytic activity assays of representative enzymes isolated from the charge engineered libraries. A) Variants from DNA library—50 μl of culture supernatant from induced cultures of monoclonal yeast populations were combined with 150 μl of 0.75 mg/ml UV inactivated *Micrococcus luteus* and 30 μM propidium iodide in 10 mM sodium phosphate buffer pH 6.0. Duplicate assays were run in the presence (white bars) and absence (black bars) of 1% wt/vol alginate. Activities were normalized to enzyme expression levels, as evaluated by sodium dodecyl sulfate polyacrylamide gel electrophoresis. Note the complete inhibition of wild type human lysozyme [WT-LYZ] by 1% alginate. Also note that charge engineered enzyme 2-3-7 exhibits lytic activity exceeding that of wild type human lysozyme both in the presence and absence of alginate inhibitor. The latter is an unanticipated but particularly beneficial outcome. B) Variants from external quality assessment (EQA) library—50 μl of culture supernatant from induced cultures of monoclonal yeast populations were combined with 150 μl of 0.75 mg/ml UV inactivated *Micrococcus luteus* and 5 μM SYTOX® Green (Molecular Probes, Eugene, Oreg.) in 10 mM sodium phosphate buffer pH 6.0. Duplicate assays were run in the presence (white bars) and absence (black bars) of 0.5% wt/vol alginate. Activities were normalized to enzyme expression levels. A sample of 50 ng commercially produced human lysozyme [50 ng USB] (US Biologicals, Swampscott, Mass.) was included in the analysis. Note that in the presence of 0.5% alginate, wild type human lysozyme culture supernatant [WT-LYZ] retains only 5% of its activity and the US Biologicals produced wild type human lysozyme retains only 2.5% of its activity. Also note that charge engineered enzymes D7, D9, F9, F10 and A3 exhibit lytic activity exceeding that of wild type human lysozyme both in the presence and absence of alginate inhibitor. The latter is an unanticipated but particularly beneficial outcome.
Figure 2B:
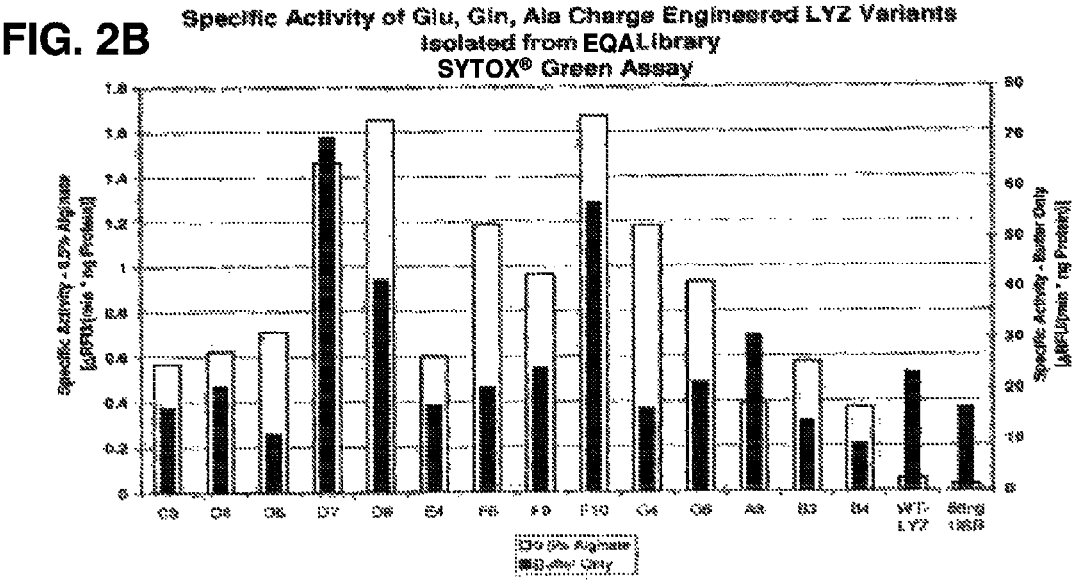

Modern protein engineering technologies have the capacity to solve these types of complex molecular engineering problems by applying iterative evolutionary algorithms that combine cutting edge DNA diversification techniques with carefully designed high throughput functional screens (29). To facilitate a combinatorial approach to engineering a human lysozyme with enhanced therapeutic activity in the presence of polyanionic inhibitors, a customized functional screen (described in Example 1) was developed. The screen allows moderately sized recombinant lysozyme libraries (up to a few million members) to be exhaustively assayed in a few days' time. This plate-based screen tests for hydrolytic activity towards peptidoglycan in the presence of any desired additive, including anionic biopolymers such as DNA, mucin, actin, heparin and alginate (hereafter collectively referred to as polyanion inhibitors)(data not shown). In addition to polyanionic additives, the assay has sufficient flexibility to mimic other key attributes of the inflamed lung environment (e.g., temperature, ionic strength, pH, etc.). This customized screen is generally applicable to screening a variety of recombinant lysozyme libraries, and is particularly useful for screening designed libraries of charge mutant human lysozymes. Provided herein are lysozyme variants whose antimicrobial activity in the presence of polyanion inhibitors far exceeds that of the wild type protein. As a further unexpected outcome, many of the engineered enzymes exhibit lytic activity exceeding that of the wild type enzyme in the absence of polyanion inhibitors (FIG. 2A and FIG. 2B). Such enzymes are particularly attractive therapeutic candidates, as they would likely find broad utility in treating a wide spectrum of microbial or viral infections.

Lysozyme Variants

The present invention relates to a group of genetically engineered lysozyme variants that exhibit enhanced antimicrobial activity under conditions of clinical relevance, particularly in the presence of polyanion inhibitors. The invention further relates to the use of these genetically engineered proteins as therapeutic agents for treating microbial or viral infections, particularly (but not exclusively) bacterial infections of the respiratory tract. The engineered enzymes are isolated from large combinatorial libraries using customized plate based functional screens.

As used herein, the term "enhanced activity" means increased activity. The term "enhanced activity" is meant to encompass also the improvement of antimicrobial activity of the modified enzyme compared to its wild type. For example, in one embodiment, the modified enzyme exhibits enhanced antimicrobial activity in the presence of alginate. In one embodiment, the enzyme has at least 2-fold, 3-fold, or 4-fold increased IC50 for alginate. As another example, the lysozyme protein exhibits enhanced antimicrobial activity in the presence of DNA. In one embodiment, the enzyme has at least 10, at least 20, at least 30, at least 40, or at least 50-fold increased IC50 for DNA. In another embodiment, the enzyme has at least 43-fold increased IC50 for DNA.

In another embodiment, the lysozyme enzyme exhibits enhanced antimicrobial activity in the presence of mucin. In one embodiment, the enzyme has at least 2-fold, 3-fold, 4-fold, 5-fold, 6-fold, 7-fold, 8-fold 9-fold or 10-fold, increased IC50 for mucin. In one embodiment, the enzyme has at least 6-fold increased IC50 for mucin.

By designing the customized plate screen to mimic desired clinically relevant aspects of pathogenic microbial or viral infections, a variety of engineered lysozymes with improved therapeutic antimicrobial activity may be isolated. In general, the plate screen consists of i) a solid nutrient media containing all media components required for growth of the recombinant expression host and induction of lysozyme expression, ii) imbedded within this growth media non-viable bacterial reporter cells or cell wall peptidoglycan isolated from a desired bacterial target, iii) if desired, molecules or species known to inhibit the therapeutic activity of lysozyme. The presence of the non-viable reporter bacteria and/or associated peptidoglycan causes bulk phase turbidity of the solid growth media. Recombinant expression hosts, especially yeast cells, producing lysozyme variants encoded by a recombinant gene library are plated on this growth media. Those expression hosts producing and secreting a lysozyme variant able to hydrolyze the peptidoglycan present in the bulk phase media (as either purified peptidoglycan or non-viable cells) develop a visible zone of clearance, or halo, in the media immediately surrounding the colony (data not shown). Yeast cells producing the largest zones of clearance can be isolated and propagated for subsequent lysozyme gene purification, thus linking genotype (mutated lysozyme gene) to phenotype (high level hydrolytic activity). In addition to supporting growth of recombinant host cells, the solid media may contain additives that serve to mimic the biological environment of bacterial infections. In particular, as detailed herein, such additives include DNA, mucin, actin, heparin and/or alginate (data not shown). These inhibitory polyanions are found in high concentrations in the lungs of patients with lower respiratory tract infections.

The customized plate screen described above may be used for high throughput screening of lysozyme libraries for the purpose of isolating variants exhibiting enhanced levels of antimicrobial activity under the conditions of interest. DNA libraries encoding mutated lysozymes can be constructed using a variety of recombinant DNA technologies that are well-known to those skilled in the art (30). Following construction of a lysozyme gene library, cloning of the gene library into a suitable expression plasmid, and transformation of that plasmid library into a recombinant expression host, the cellular library (each cell producing one unique protein sequence) can be plated on the indicating media to facilitate spatial separation of the diverse cell population. Incubation of the indicating media at an appropriate temperature will result in outgrowth of the recombinant host cell residing on top of the nutrient medium (data not shown). Should the media include a chemical inducer for expression of the recombinant lysozyme, the recombinant host cell colonies will produce their encoded variant proteins and secrete those proteins into the extracellular space. The secreted proteins will diffuse into the medium where they may or may not interact with inhibitory additives included in medium formulation (data not shown). Should any particular lysozyme not be inhibited or sequestered by the additives in the medium, it will continue to diffuse into the medium, which contains the embedded non-viable indicator bacteria or peptidoglycan derived from the same. Should a particular protein that avoids inhibition or sequestration in the medium have the capacity to hydrolyze the peptidoglycan of the indicator bacteria, that protein will result in a zone of clearance easily identified against the background of embedded non-viable indicator cells or peptidoglycan derived from the same (data not shown). Due to diffusion limitations, this zone of clearance will be restricted to the local space around the recombinant host cell expressing that particular protein.

Upon identification of a recombinant host cell colony with a surrounding zone of clearance, the recombinant host cells of that colony can be individually harvested and grown as a monoclonal culture. This monoclonal culture provides a source for isolating the mutant gene encoding the highly active antimicrobial lysozyme, and can also serve as a stock from which to carry out large scale liquid culture expression of the highly active lysozyme variant for further studies.

The isolated lysozyme variants constitute therapeutic antimicrobial protein candidates by virtue of their improved activity under conditions of clinical relevance, e.g. in the presence of polyanion inhibitors. The plate screen, described above, for isolating the engineered lysozymes is distinct from that described in WO 2004/033715 A1 in that the former expressly uses non-viable reporter bacteria or peptidoglycan purified from said bacteria while the latter explicitly, and as an essential element of its implementation, describes growth inhibition of viable reporter bacteria. The use of non-viable reporter bacteria and/or purified peptidoglycan from the same is a necessary element of the screen described herein, as it has been found that use of metabolically active reporter bacteria inhibit the growth of recombinant yeast cells and prevent production of sufficient lysozyme quantities (Scanlon and Griswold, unpublished data).

The engineered enzymes isolated using the screen described here exhibit dramatically improved and therapeutically relevant activities, relative to the wild type enzyme. Said engineered enzymes may be administered to subjects as therapeutic agents for treating bacterial, fungal or viral infections. Said administration may be accomplished by inhalation of the enzyme in nebulized solutions, aerosolized liquids or powders, or microencapsulated droplets. Alternatively, the enzymes may be applied topically, injected via syringe or other apparatus, ingested orally, or inserted as a suppository.

Preferred embodiments of the lysozyme variants provided herein are shown below in Table 1. The lysozyme variants can be referred to herein as "compositions of the invention," "compounds of the invention," "enzymes of the invention," "proteins of the invention," "lysozymes of the invention," etc.

In another embodiment, provided herein is a method of treating respiratory infection in a subject in need thereof comprising administering to the subject an effective amount of one or more of the lysozyme variants provided herein (e.g., the variants having the sequences provided in the attached Sequence Listing), such that the respiratory infection is treated. In another embodiment, provided herein is a method of treating respiratory infection in a subject in need thereof comprising administering to the subject an effective amount of lysozyme variant 2-3-7 (SEQ ID NO: 1 in the attached Sequence Listing), such that the respiratory infection is treated. In another embodiment, provided herein is administration of a suitable amount of lysozyme variant 2-3-7 (SEQ ID NO: 1 in the attached Sequence Listing) by inhalation via nebulizer or other appropriate device. In certain embodiments, the variants described herein are human lysozyme variants.

In another embodiment, provided herein is a method of treating viral infection in a subject in need thereof comprising administering to the subject an effective amount of one or more of the lysozyme variants provided herein (e.g., the variants having the sequences provided in the attached Sequence Listing), such that the respiratory infection is treated. In another embodiment, provided herein is a method of treating viral infection in a subject in need thereof comprising administering to the subject an effective amount of lysozyme variant 2-3-7 (SEQ ID NO: 1 in the attached Sequence Listing), such that the viral infection is treated.

Methods of Treatment

Compounds of the present invention are useful for the treatment of microbial and viral infections in a subject.

As used herein, the term "microbial or viral infection" refers to the invasion of the host animal by pathogenic microbes or viruses. This includes the excessive growth of microbes or viruses that are normally present in or on the body of a subject. More generally, a microbial or viral infection can be any situation in which the presence of a microbial or viral population(s) is damaging to a host animal. Thus, a subject is "suffering" from a microbial or viral infection when excessive numbers of a microbial or viral population are present in or on an animal's body, or when the presence of a microbial or viral population(s) is damaging the cells or other tissue of an animal.

The term "microbes" includes, for example, bacteria, fungi, yeasts, protozoa, parasites. The term "virus" includes infectious agents that can only replicate inside another organism, and can be DNA or RNA viruses.

Non-limiting examples of microbial and viral infections include infectious diseases of the respiratory system (e.g., pneumonia, typical pneumonias, atypical pneumonias, common cold, diphtheria, influenza, histoplasmosis, strep throat, tuberculosis, lung abscess, acute bronchitis, emphysema, and others), infectious diseases of the skin and eyes (e.g., abscess, acne, boil, Candidiasis, Carbuncle, chickenpox, cold sores, fever blisters, folliculitis, furuncle, genital herpes, German measles, impetigo, measles, oral herpes, pimple, Ringworm, Rubella, scabies, scalded skin syndrome, shingles, smallpox, sty, thrush, toxic shock syndrome, trachoma, varicella, variola, warts, zosters, and others), localized infections of the skin (e.g., abscess, boil, carbuncle, folliculitis, furuncle, pimple, sty and others), infectious diseases of the nervous system (e.g., bacterial meningitis, botulism, encephalitis, Leprosy, Meningitis, Poliomyelitis, rabies, tetanus, and others), infectious diseases of the cardiovascular and lymphatic systems (e.g., black death, blood poisoning, bubonic plague, childbirth fever, epidemic typhus, gas gangrene, Lyme disease, Lymphangitis, malaria, mononucleosis, plague, puerperal sepsis, Rocky Mountain spotted fever, Septicemia, septic shock, and others), infectious diseases of the digestive system (e.g., dysentery, Giardiasis, hepatitis B, staphylococcal food poisoning, peptic disease syndrome, and others), and infectious diseases of the urinary and reproductive systems (e.g., genital herpes, genital warts, gonorrhea, nongonococcal urethritis, pelvic inflammatory disease, syphilis, and others). Other examples of microbial or viral infections include HIV/AIDS, diarrheal diseases, malaria, measles, pertussis, tetanus, meningitis, tropical diseases (e.g., Chagas disease (American trypanosomiasis), African trypanosomiasis (sleeping sickness), Leishmaniasis, Leprosy (Hansen's diseases), Lymphatic filariasis, Onchocerciasis (river blindness), Schistosomiasis (snail fever or schisto), sexually transmitted infections, Hookworm, Trichuriasis, Treponematoses, Buruli ulcer, Dracunculiasis, Leptospirosis, Strongyloidiasis, Foodborne trematodiases, Scabies, Flavivirus infections, Ebola hemorrhagic fever, Lassa fever, the Marburg hemorrhagic fever and others).

Microbial or viral infections that can be treated by the lysozyme variants described herein can also be related to the activity or proliferation of *Micrococcus luteus, Pseudomonas aeruginosa, Staphylococcus aureus, Klebsiella pneumoniae*, or *Saccharomyces cerevisiae* in a subject. The microbial or viral infection can also be related to the activity or proliferation of gram-positive or grans negative bacteria.

The term "treat," "treated," "treating" or "treatment" includes the diminishment, alleviation, or amelioration of at least one symptom associated or caused by the state, disorder or disease being treated. In certain embodiments, the treatment comprises the induction of a microbial or viral infection, followed by the activation of the composition of the invention, which would in turn diminish or alleviate at least one symptom associated or caused by the microbial or viral infection being treated. For example, treatment can he diminishment of one or several symptoms of a disorder or complete eradication of a disorder.

The term "use" includes any one or more of the following embodiments of the invention, respectively: the use in the treatment of microbial or viral infections; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from microbial or viral infections, e.g. respiratory infections, as well as those diseases that depend on the activity of microbes or viruses.

The term "subject" is intended to include organisms, e.g., prokaryotes and eukaryotes, that are capable of suffering from or afflicted with a disease, disorder or condition associated with microbial or viral infections. Examples of subjects include mammals, e.g., humans, dogs, cows, horses, pigs, sheep, goats, cats, mice, rabbits, rats, and transgenic non-human animals, in certain embodiments, the subject is a human, e.g., a human suffering from, at risk of suffering from, or potentially capable of suffering from microbial or viral infections, and other diseases or conditions described herein. In another embodiment, the subject is a cell.

Pharmaceutical Compositions

The compositions of the present invention are suitable as active agents in pharmaceutical compositions that are efficacious particularly for treating microbial or viral infection, e.g., respiratory infection. The pharmaceutical composition in various embodiments has a pharmaceutically effective amount of the present active agent along with other pharmaceutically acceptable excipients, carriers, fillers, diluents and the like.

The language "pharmaceutically effective amount" of the compound is that amount necessary or sufficient to treat or prevent a microbial or viral infection, e.g. prevent the various morphological and somatic symptoms of a microbial or viral infection, and/or a disease or condition described herein. In an example, an effective amount of a compound of the invention is the amount sufficient to treat a microbial or viral infection in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. A compound of the invention can be administered to the subject either prior to or after the onset of a microbial or viral infection. Further, several divided dosages, as well as staggered dosages can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

The phrase "pharmaceutically acceptable amount" of a compound of the present invention refers to an amount of a compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the phrase "pharmaceutically acceptable amount" refers to the amount of a compound of the present invention that, when administered to a subject, is effective to (1) at least partially alleviate, inhibit, prevent and/or ameliorate a condition, or a disorder or a disease (i) mediated by microbes or viruses, or (ii) associated with microbes or viruses, or (iii) characterized by abnormal activity of microbes or viruses; or (2) reduce or inhibit the activity of microbes or viruses. In another non-limiting embodiment, the phrase "pharmaceutically acceptable amount" refers to the amount of a compound of the present invention that, when administered to a subject, is effective to at least partially, alleviate, inhibit, prevent and/or ameliorate a microbial or viral infection. In still another non-limiting embodiment, the term "pharmaceutically acceptable amount" refers to the amount of a compound of the present invention that, when administered to a cell, or a tissue, or a non-cellular biological material, or a medium, is effective to at least partially reduce or inhibit the activity of one or more microbes or viruses; or at least partially reduce or inhibit the expression of one or more microbes or viruses.

The acceptable amount can vary depending on such factors as the size and weight of the subject, the type of illness, or the particular organic compound. For example, the choice of the organic compound can affect what constitutes an "acceptable amount." One of ordinary skill in the art would be able to study the aforementioned factors and make the determination regarding the acceptable amount of the organic compound without undue experimentation.

Compounds of the invention may he used in the treatment of states, disorders or diseases as described herein, or for the manufacture of pharmaceutical compositions for use in the treatment of these diseases. Methods of use of compounds of the present invention include the treatment of these diseases, or pharmaceutical preparations having compounds of the present invention for the treatment of these diseases.

Also provided herein is a pharmaceutical composition comprising a lysozymes of the invention and a pharmaceutically acceptable carrier. The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can he used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl, alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metal hydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients on carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, snick acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate, Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like, it may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled, Examples of other biodegradable polymers include poly(orthoesters) and poly(anhydrides). Depot injectable formulations are also prepared by entrapping the drug in liposomes or microemulsions that are compatible with body tissue.

The preparations of the present invention may be given orally, parenterally topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The compositions of the invention can be systemically administered to a subject in need thereof. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by, conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will he that amount of the compound that is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more. preferably from about 1.0 to about 100 mg per kg per day. An effective amount is that amount treats a microbial or viral infection, e.g., respiratory infection.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Specific embodiments of the present invention are described in greater detail by the following non-limiting examples.

Example 1: Construction of Combinatorial Lysozyme Charge Mutant Library

As discussed herein, lysozyme is inactivated in the inflamed lung through aggregation with inhibitory polyanions (FIG. 1, as well as other data not shown), a process driven by coulombic attraction between the oppositely charged species. To disrupt this electrostatic attraction, surface-exposed basic amino acid residues are mutated to uncharged polar (glutamine, asparagine), uncharged nonpolar (alanine), or negatively charged (glutamic acid, aspartic acid) residues in a combinatorial fashion. Wild type human lysozyme possesses 14 arginines, 5 lysines and one histidine residue in surface exposed positions. A bioinformatics analysis was conducted on these basic residues to identify those that are poorly conserved among 50 different C-type lysozymes from other mammalian species (ConSurf-Server: Phylogenetic Surface Mapping, (31)). Using a combined scoring function based on degree of evolutionary conservation (less conserved better), proximity to the active site (more distal to the active site better) and general structural inspection (identifying residues whose side chains orient away from the active site and seeking an even spatial distribution of mutagenized residues), 8 of the 20 basic residues were defined as "permissive" sites for mutagenesis (Arginines 14, 21, 41, 50, 101, 115, 119, 122, and Histidine 78). The codons for these residues were combinatorially mutated to generate two different libraries wherein the target codons were changed to either i) glutamic acid, glutamine, or alanine codons (EQA library), or ii) aspartic acid, asparagine, or alanine codons (DNA library). The mutagenesis is accomplished using an ISOR based approach known in the art (32). Briefly, a diverse pool of mutant genes is constructed by DNase I fragmentation of the wild type lysozyme coding sequence and reassembly of the resulting gene fragments in the presence of synthetic mutagenic primers encoding mutations at the desired positions. The resulting EQA and DNA gene libraries are composed of 65,536 unique sequences each (eight sites with four possible codons at each site, including wild type arginine or histidine codons). As an aside, the apparent impurities in the Arg115 mutant primers resulted in unexpected incorporation of a histidine codon at residue 115 for some clones in the DNA library. The incorporation of histidine was unexpected but adventitious for many variants, e.g. variant 2-3-7, A111, C13, G15, G18, A26, E29, G211, C25, D25 and D27 (see below). The mutant gene library is cloned into a modified version of an inducible yeast expression vector wherein the 5'-end of the lysozyme gene is fused to a prepro sequence for alpha mating factor such that lysozyme expression and secretion into the extracellular space may be induced with a suitable additive. The plasmid libraries are transformed into *Saccharomyces cerevisiae* expression hosts yielding a cellular library wherein each yeast cell contains recombinant DNA encoding one unique mutant lysozyme gene. Induction of protein expression from these yeast results in expression and secretion of a highly diverse lysozyme variant library wherein each protein possesses unique functional properties.

Example 2: Functional Screening of Lysozyme Charge Mutant Library

Recombinant yeast expressing variant lysozyme proteins are plated on agarose-based solid nutrient media containing the polyanion inhibitor alginate and heat-killed *Micrococcus luteus* as the indicator bacteria. The plates are then incubated at 30° C., a temperature suitable for yeast growth and protein expression. The diverse population of proteins encoded by, the EQA and DNA libraries span the continuum of electrostatic character from the wild-type enzyme's +7.7 charge to the −7.3 charge of the octuple Arg-to-Asp or Arg-to-Glu mutants (at physiological pH). Among this population of mutated proteins, it is contemplated that many proteins will be inactivated by failure to fold properly, some proteins will fold but continue to be sequestered by the polyanion inhibitors, some proteins will escape sequestration by polyanion inhibitors but will lose antimicrobial activity as a result of mutation, and a few proteins will exhibit both reduced affinity for the polyanion inhibitors and high levels of antimicrobial activity. Yeast colonies expressing these latter enzymes are easily identified by their phenotypic zone of clearance. These colonies are harvested, and the amino acid composition of the cognate proteins is deduced by sequencing the respective genes. This plate-based functional screen is suitable for screening libraries of up to a few million clones in a matter days.

It is further contemplated that a variety of experimental variables can be modulated to adjust the assay's dynamic range so that only the most active clones are able to generate zones of clearance. Examples of parameters that can be adjusted to optimize the screen include concentration of non-viable indicator cells or peptidoglycan, lysozyme expression levels, incubation times and temperature, and the nature/concentration of polyanion additives in the plates.

The EQA and DNA libraries disclosed above have been screened, as described, by plating on agarose-based CSM-uracil dropout nutrient media containing 100 mM sodium phosphate pH 6.0, the polyanion inhibitor alginate (0.1% to 3% wt/vol), 0.67% yeast nitrogen base, 0.05% wt/vol galactose, 1.95% wt/vol raffinose, and 0.5 mg/ml heat-killed *Micrococcus luteus* as the indicator bacteria. Yeast clones producing enzyme variants exhibiting enhanced peptidoglycan hydrolyzing activity in the presence of the alginate inhibitor have been isolated. Specifically, the selected yeast clones expressing charge engineered therapeutic candidates produce zones of clearance substantially larger than that of yeast clones expressing wild type human lysozyme when plated on indicating medium containing heat-killed *Micrococcus luteus* and the inhibitory biopolymer alginate (data not shown). The identities of the amino acids at the eight mutagenized enzyme residues are provided for some of the functionally improved variants (Table 1). The full amino acid sequences of these variants are provided in the attached electronic Sequence Listing File.

Table 1 shows the amino acid identity of the engineered enzymes isolated using the plate based functional screen. The eight residues targeted for mutagenesis are noted by number at the top of the table (numbered from lysine 1 of mature human lysozyme). All other residues not listed correspond to those of wild type human lysozyme, as verified by sequence analysis. The one letter codes for the amino acids identities at the target sites are given in the table. At the right of the table is the charge of each protein at pH 7 (rounded to the nearest whole number) and the change in charge relative to the wild type human enzyme, The full sequences of 31 candidate therapeutic enzymes are provided in the attached electronic Sequence Listing.

TABLE 1

| | Residue Number (numbering from Lys 1 of wild type human lysozyme) | | | | | | | | | Delta from |
|---|---|---|---|---|---|---|---|---|---|---|
| Clone | 14 | 21 | 41 | 50 | 78 | 101 | 115 | 122 | Charge | WT |
| Wild Type | R | R | R | R | H | R | R | R | +8 | 0 |
| 2-1-1 | D | A | D | R | H | R | R | R | +3 | −5 |
| 2-1-2 | N | A | D | R | H | R | R | R | +4 | −4 |
| 2-3-1 | A | R | R | R | D | D | A | A | +2 | −6 |
| 2-3-2 | D | A | D | D | H | R | D | R | −1 | −9 |
| 2-3-3 | R | R | R | R | H | D | A | R | +5 | −3 |
| 2-3-4 | R | R | R | R | D | A | N | R | +5 | −3 |
| 2-3-5 | A | R | R | R | D | R | R | R | +6 | −2 |
| 2-3-7 | R | R | R | R | H | D | H | R | +5 | −3 |
| 2-3-8 | N | A | R | R | H | R | R | A | +5 | −3 |
| 2-3-9 | A | N | R | D | N | D | R | R | +2 | −6 |
| 2-3-10 | A | A | R | A | H | R | R | R | +4 | −4 |
| 2-3-11 | A | A | R | R | A | A | R | D | +3 | −5 |
| 2-3-12 | N | A | R | R | D | R | N | R | +4 | −4 |
| 2-5-1 | A | N | R | R | A | R | R | R | +6 | −2 |
| D9 | R | R | Q | Q | Q | R | Q | R | +5 | −3 |
| E4 | E | A | R | Q | Q | R | R | R | +5 | −3 |
| F10 | R | R | R | A | Q | R | Q | R | +6 | −2 |
| G6 | A | A | Q | R | H | R | Q | R | +4 | −4 |
| D7 | R | R | R | R | Q | A | R | R | +7 | −1 |

TABLE 1-continued

| Clone | Residue Number (numbering from Lys 1 of wild type human lysozyme) 14 | 21 | 41 | 50 | 78 | 101 | 115 | 122 | Charge | Delta from WT |
|---|---|---|---|---|---|---|---|---|---|---|
| F8 | E | A | Q | R | H | R | R | R | +4 | −4 |
| G4 | A | A | E | R | Q | R | R | R | +4 | −4 |
| A3 | R | R | R | A | Q | A | R | R | +6 | −2 |
| B3 | Q | Q | R | A | A | R | R | R | +5 | −3 |
| B4 | Q | A | R | E | R | Q | R | R | +3 | −5 |
| C3 | A | Q | Q | R | A | R | R | R | +5 | −3 |
| C6 | R | R | Q | Q | A | Q | R | R | +5 | −3 |
| D6 | E | A | Q | R | Q | R | R | R | +4 | −4 |
| F9 | Q | A | Q | Q | E | E | R | R | +1 | −7 |
| A111 | A | A | E | R | Q | R | H | R | +3 | −5 |
| C13 | E | Q | R | R | Q | R | H | R | +4 | −4 |
| G15 | N | A | Q | R | Q | R | H | R | +4 | −4 |
| G18 | A | A | Q | R | Q | R | H | R | +4 | −4 |
| A26 | A | Q | Q | R | Q | R | H | R | +4 | −4 |
| G211 | A | A | Q | R | A | R | H | R | +4 | −4 |
| C25 | E | R | R | R | H | A | H | R | +4 | −4 |
| D25 | A | A | R | A | Q | R | H | R | +4 | −4 |

Example 3: Validation of Selected Enzymes Characterization of Antimicrobial Activity Rank Ordering Enzymes by Lytic Activity.

To validate and rank order the lytic activity of the selected enzymes, clones isolated from the primary screen (indicating plates) are inoculated into liquid media. The yeast cells are grown in liquid media as monoclonal populations, and expression/secretion of their respective lysozyme proteins is induced with galactose. Subsequently, the cells are pelleted by centrifugation, and culture supernatants are used in turbidometric assays of lytic activity towards *Micrococcus luteus*. Briefly, turbid suspensions of UV irradiated or otherwise inactivated *Micrococcus* bacteria in phosphate buffer are combined with physiologically relevant concentrations of DNA, mucin, actin, heparin, alginate, or combinations thereof. These assay solutions are then aliquoted to clean microtiter plates and mixed with culture supernatants from the induced yeast cells. The lytic activity of the variant lysozymes is followed by monitoring light scatter of the suspensions at 450 nm and/or 600 nm (lysis of the particle-like bacteria reduces light scatter proportionally). Because 96 different enzymes can be assayed simultaneously, up to a few thousand clones per day can be evaluated using this method. The lytic activity of different yeast cell cultures are normalized to lysozyme expression levels as evaluated by digital image analysis (Quantity One Software, Biorad) of SDS-PAGE gels stained with COOMASSIE BRILLIANT BLUE™ or other suitable protein dyes. These normalized activities are rank ordered, and the most active enzymes are selected for further characterization. To increase the sensitivity of the assay, DNA intercalating fluorophores such as propidium iodide or SYTOX® green (Molecular Probes, Eugene, Oreg.) may be used to monitor hydrolysis of bacterial cell wall peptidoglycan (FIG. 2A and FIG. 2B). The fluorophores exhibit low fluorescence when alone in aqueous solution, but their fluorescence intensity increases markedly upon intercalation into double stranded DNA. The fluorophores are unable to pass through intact *Micrococcus* cell walls (UV inactivation does not significantly compromise cell wall impermeability), but hydrolysis of a portion of the cell wall peptidoglycan renders the cell wall permeable to the fluorophores. Note that the DNA intercalating fluorophores are not compatible with DNA as an inhibitory polyanion.

Using these turbidometric and fluorescence assays, it has been demonstrated that not only do the engineered enzymes exhibit drastically improved lytic activity in the presence of polyanion inhibitors, but many of the modified proteins exhibit lytic activity exceeding that of wild type human lysozyme in standard 10 mM sodium phosphate buffer alone (FIG. 2A and FIG. 2B). The improved activity in the absence of polyanion inhibitors is a surprising and unexpected result. This unanticipated functional improvement of the engineered enzymes contributes significantly to the novelty and the therapeutic potential of the disclosed invention, as it suggests that the enzymes disclosed herein are likely to represent improved antimicrobial and therapeutic agents under a vast array of clinical conditions beyond the anticipated presence of polyanionic inhibitors in the infected lung.

Purification and Detailed Biochemical characterization of Promising Candidates.

The ten to twenty most active enzymes as determined by the turbidometric and fluorescence assays are expressed on a 1 L scale and purified from culture supernatants using standard techniques, such as cation exchange chromatography. The purified enzymes are analyzed by a turbidometric assay similar to that described above, allowing determination of cell lysis kinetics for the purified proteins. Additionally, the bactericidal properties of the purified enzymes towards *Micrococcus luteus* and clinical isolates of *Staphylococcus aureus, Kiebsiella pneumoniae*, and *Pseudomonas aeruginosa* may be determined by a modification of conventional quantitative culture assays (33) in which physiologically relevant concentrations of DNA, mucin, actin, heparin and/or alginate are incorporated in the cell suspensions. Bactericidal activity toward the various pathogens is quantitated by determination of colony forming units relative to negative control samples (no lysozyme).

The quantitative analysis of the engineered enzymes' kinetics and their antimicrobial activities toward pathogenic bacteria under conditions that replicate aspects of the infected lung provides clinically relevant data regarding the therapeutic potential of the isolated enzymes. Charge-engineered LYZ variants were found to possess superior antibacterial activity when compared to the natural WT-LYZ sequence. To measure the fold improvement of charge-engineered variants, kinetic measurements of hydrolysis of freeze-dried cells of *Micrococcus luteus* was performed.

Charge-engineered LYZ variants were found to possess significant improvements in antibacterial activity compared to the WT-LYZ enzyme in the presence of polyanion molecules resident in the inflamed lung. To quantify this improvement, the concentration of polyanion that inhibits enzyme activity 50% ($IC_{50}$) was measured for both WT-LYZ and the variant 2-3-7 in a microplate format. The mutant 2-3-7 is superior to the WT-LYZ for all polyanions tested with a fold increase in $IC_{50}$ for DNA, mucin and alginate of 43.3, 6.91 and 3.13, respectively (Table 2).

Table 2 shows the results of kinetic characterization of WT-LYZ and the best variant 2-3-7. Lytic activity of WT-LYZ and mutant 2-3-7 were determined in 96-well format by monitoring the decrease in absorbance at 450 nm of a solution of UV-inactivated, freeze-dried *Micrococcus luteus* cell walls over a wide range of concentrations. The apparent $K_m$ of WT-LYZ was measured to be 100 μg/mL with a $V_{max}$ value of 900 $\Delta A_{450nm}$/min*mg while the mutant 2-3-7 had an apparent $K_m$ of 40 μg/mL and a $V_{max}$ value of 720 $\Delta A_{450nm}$/min*mg.

TABLE 2

| Enzyme | Vmax [DA450]/ (min*mg) | KmApp (μg/mL) | Vmax/ KmAPP | IC50 – Alginate (μg/mL) | IC50 – Mucin (μg/mL) | IC50 – DNA (μg/mL) |
|---|---|---|---|---|---|---|
| LYZ | 900 ± 100 | 100 ± 30 | 9 | 36 | 11 | 31 |
| 237 | 720 ± 50 | 40 ± 10 | 18 | 115 | 73 | 1336 |

Figure 3:
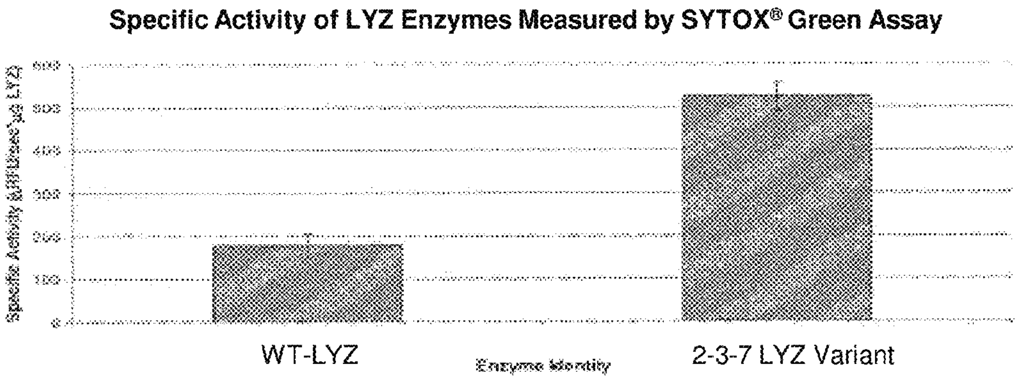
FIG. 3 shows the specific activity of WT-LYZ and variant 2-3-7 as measured by the SYTOX® Green Membrane Permeability Assay. Fifty nanograms of each enzyme variant were added to 250 μl reactions containing 0.75 mg/ml UV-inactivated *Micrococcus luteus* and 5 μM SYTOX® Green (Molecular Probes, Eugene, Oreg.) in 66 mM potassium phosphate buffer, pH 6.24. Fluorescence intensity is proportional to the ability of each enzyme to rupture the bacterial cell wall and allow the SYTOX® Green dye access to the bacterial DNA. This is in contrast to absorbance-based methods that require complete lysis of target bacteria for signal detection. In contrast, signal generation with the fluorogenic assay should require only sufficient peptidoglycan hydrolysis to disrupt the cell wall's function as a diffusional barrier. Considering sub-lytic cell wall damage is sufficient to kill bacteria, the Permeability Assay is likely a better metric for antibacterial activity. The rate of increase in fluorescence per second was divided by enzyme quantity in the assay to generate the specific activity metric. At this high concentration of substrate (>>$V_{max}$ for each enzyme), there was a surprising difference in specific activity between the two enzymes. The 2-3-7 variant demonstrates a 2.5-fold increase in specific activity using this method. Without being bound by theory, it appears that this result demonstrates the superior antibiotic activity of 2-3-7 compared to the WT-LYZ.
Figure 4:
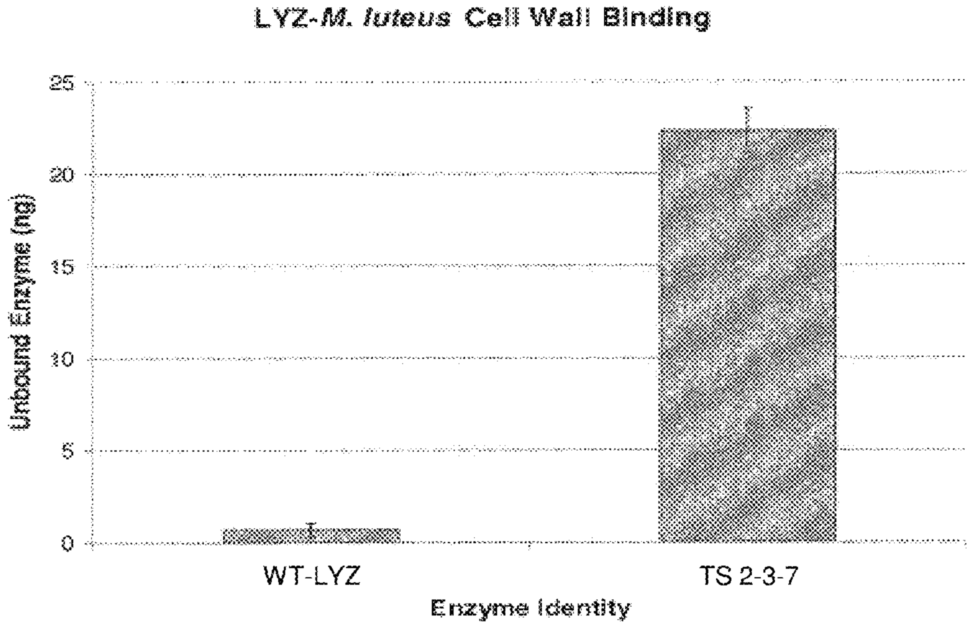
FIG. 4 shows the results of cell-wall binding of WT-LYZ and the variant 2-3-7. Two hundred nanograms of enzyme variant was added to a 1.0 ml solution of 800 μg/mL freeze-dried *Micrococcus luteus* cells in 66 mM potassium phosphate buffer, pH 6.24. The solution was mixed by rapidly inverting 3 times, and immediately centrifuged at 13,300× rpm for 45 seconds to pellet the insoluble bacterial cells and associated enzyme. Supernatant (containing unbound enzyme) was transferred to a new tube. Enzyme activity measurements were performed by absorbance-based assays, and compared to standard curves (prepared for each enzyme variant) to calculate the quantity of unbound enzyme variant. A 20•-fold increase in unbound variant 2-3-7 demonstrates this enzyme variant has reduced affinity for the *Micrococcus luteus* cell wall.
Figure 5:
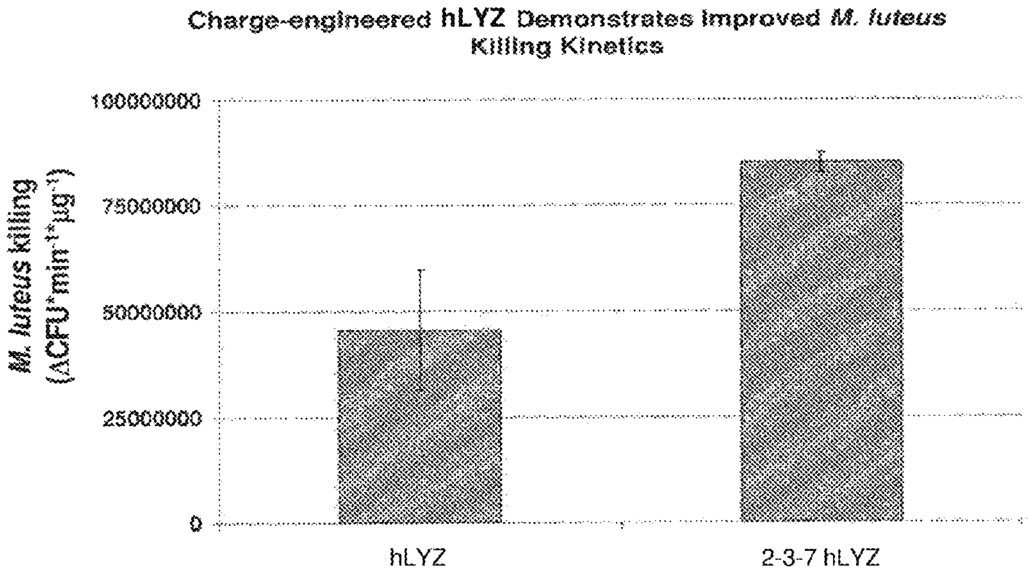
FIG. 5 and FIG. 6 show the results of enzyme treatment of mouse models of acute *Pseudomonas* infection. An oropharyngeal aspiration technique was used to inoculate the mice with mucoid *Pseudomonas* (strain FRD1) after enzyme treatment ("prophylactic treatment", FIG. 5). Alternatively, FRD1 infection was allowed to establish for 1 hour prior to enzyme therapy ("therapeutic treatment", FIG. 6). In each case, mice (n=5 for prophylactic treatment, n=6 for therapeutic treatment) were administered either PBS alone, or 20 μg of each enzyme valiant. At 24 hours post inoculation, mice were sacrificed, lungs were homogenized and the homogenate was plated on nutrient agar plates for enumeration of bacterial colony forming units (cfu), The mean was calculated for each condition and compared using the student's t-test, a p-value of 0.05 was considered significant. Note the statistically significant reduction in mucoid *Pseudomonas* infection during prophylactic treatment with 2-3-7 with respect to both PBS alone or WT-LYZ treatment.

The literature teaches that WT-LYZ is attracted to the cell wall of Gram-positive bacteria in part via electrostatic attraction between the negatively-charged cell wall of the bacteria and the positively-charged surface of the WT-LYZ enzyme (34). Consistent with this well-established principle, LYZ variants with a reduced positive-charge would be expected to exhibit reduced bacterial lysis and thus possess less therapeutic potential. An unexpected attribute of LYZ variant 2-3-7 (charge at pH 7 is approximately +5 vs. WT-LYZ at +8) is the increased specific activity of bacterial lysis (relative to WT-LYZ) at high substrate concentrations as measured by SYTOX® Green membrane permeability assay (FIG. 3). It has been hypothesized that *reduced* affinity for the bacterial cell wall enhances cellular dissociation kinetics of 2-3-7 resulting in hydrolytic activity against a larger proportion of cells in suspension. Without being bound by theory, it appears that a single WT-LYZ molecule is strongly attracted to an individual bacterium and thus remains associated with that cell beyond the point at which it has become nonviable due to cell wall permeablization. In contrast, the more transient cell association of a single 2-3-7 enzyme results in fewer postmortem hydrolytic events per bacterium, freeing that 2-3-7 enzyme molecule for subsequent attack of a distinct, viable bacterium ultimately resulting in improved killing kinetics. Consistent with this hypothesis, 21.5-fold more 2-3-7 enzyme remains unbound in the presence of an excess of *M. luteus* bacteria compared to binding of the WT-LYZ enzyme (FIG. 4). These results have important implications with respect to bactericidal activity of lysozymes modified by charge reduction. According to our new, unconventional, model of enzyme/bacteria attraction, faster specific rates of killing bacterial targets are expected of charge reduced lysozyme variants compared to wild type hLYZ. Indeed, kinetic, quantitative culture experiments performed on live *Micrococcus luteus* revealed that the charge reduced enzyme kills these bacteria approximately 2-fold faster in vitro (FIG. 5).

By screening combinatorial libraries of charge mutant lysozymes under clinically relevant conditions, new lysozyme proteins have been isolated. The unique electrostatic and antimicrobial properties that have been observed for these proteins are anticipated to result in high levels of bactericidal activity in the inflamed environment characteristic of lower respiratory tract infections.

Example 4: Evaluation in an Animal Model of Lung Infection

To determine the in vivo efficacy of the engineered lysozyme candidates in a clinically relevant system, a mouse model of *Pseudomonas aeruginosa* lung infection is employed. *P. aeruginosa* is selected because it is a common pathogen isolated from patients with cystic fibrosis or ventilator associated pneumonia, is often resistant to antibiotics, can be difficult to eradicate from the lung, and generally leads to significant morbidity, mortality and health care-related costs. The model is used to determine whether engineered lysozymes decrease bacterial burden within the lung, promote host survival, and are safe from the perspective of acute toxicity.

Figure 6:
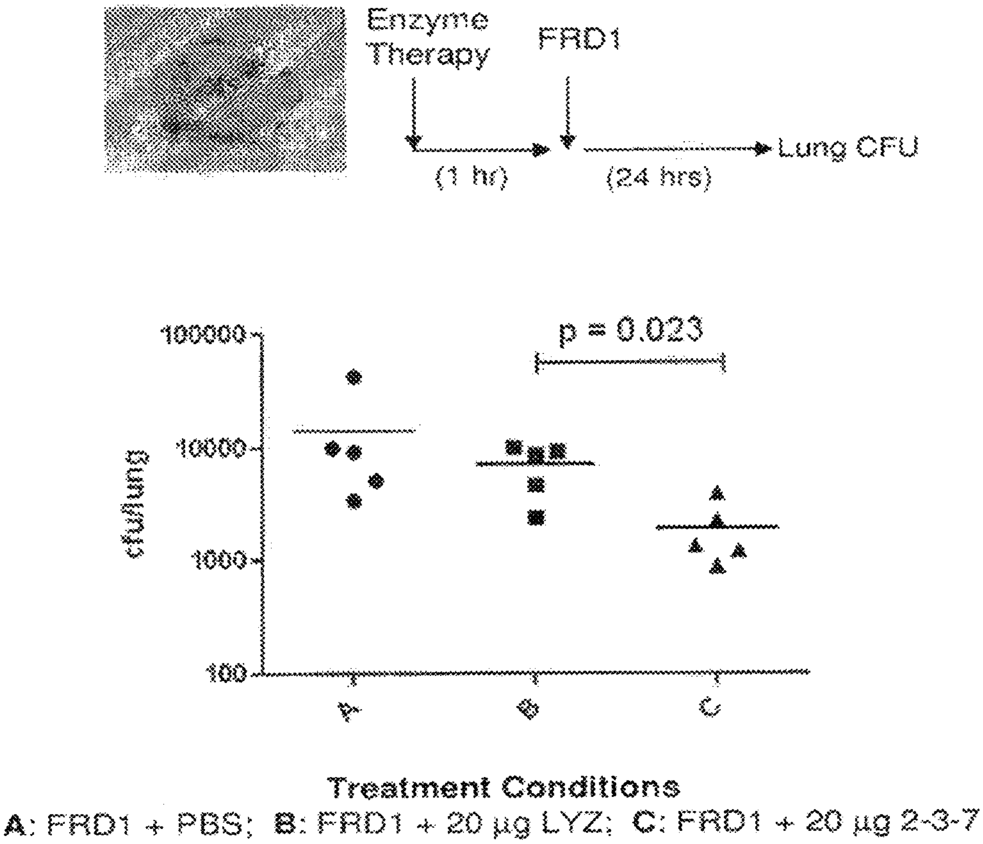
Figure 7:
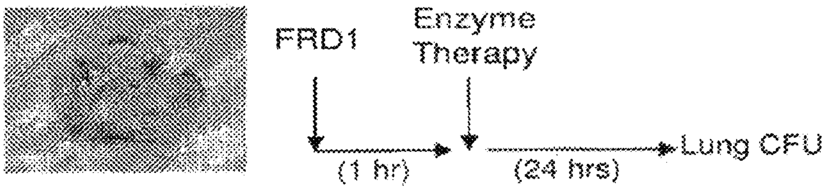
FIG. 7 demonstrates the results of enzyme treatment of a mouse model of nonmucoid *Pseudomonas* infection. Mice were inoculated with *Pseudomonas aeruginosa* strain PAO1 using the same oropharyngeal aspiration technique as described above. One hour after PAO1 infection mice (n=6) were given a dose of 2-3-7 enzyme variant (0.1 μg, 10 μg or 10 μg per mouse) to establish a dose-response relationship for enzyme treatment. Twenty-four hours after enzyme treatment, mice were sacrificed and lung tissue was homogenized. The homogenate was plated on nutrient agar, and *Pseudomonas aeruginosa* cfu were enumerated. Statistical analysis was performed as above. Note the trend towards reduction in nonmucoid *Pseudomonas* infection with increasing dose of 2-3-7 variant.
Figure 7:
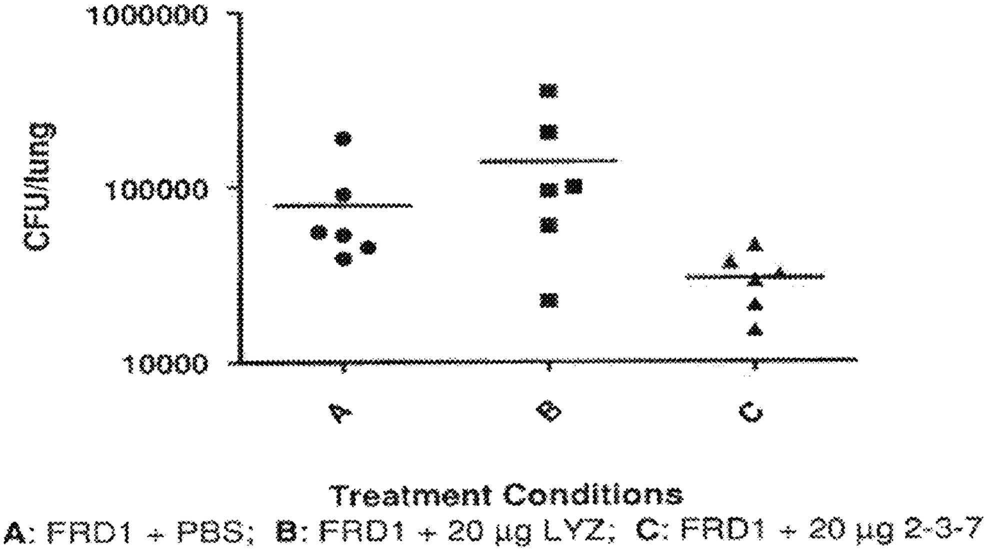
Figure 8:
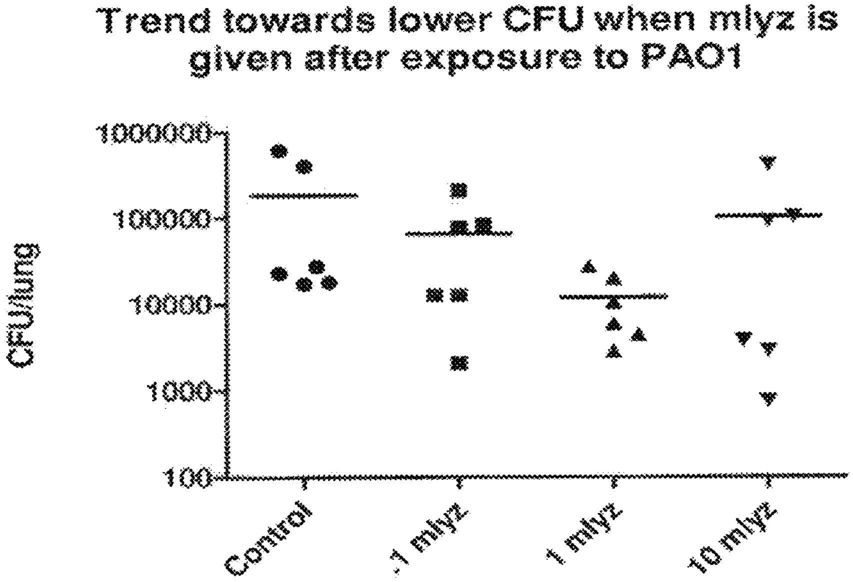
FIG. 8 shows the data described in Example 4.

Mouse models of acute pulmonary infection have been used to evaluate the in vivo therapeutic potential of a charge-engineered LYZ variant. Several dosing and treatment regimes have been performed. In one embodiment of this experimental design, mice were administered PBS only, WT-LYZ (20 μg), or charge engineered LYZ variant 2-3-7 (20 μg) in a prophylactic fashion prior to bacterial infection. One hour after administration of therapeutic, the mice were colonized with $7.75\times10^6$ CPU of mucoid *Pseudomonas aeruginosa* strain FRID1 via an oropharyngeal aspiration technique known in the art. At 24 hours post inoculation, mice were sacrificed and bacteria remaining in the lung were quantified. Treatment with 2-3-7 LYZ variant produced a statistically significant reduction in total CPU compared to both PBS alone and wild-type LYZ of similar dose (FIG. 6). In another embodiment of this experimental design, mice were inoculated with $2.9\times10^6$ CPU mucoid *Pseudomonas aeruginosa* strain FRD1 *before* treatment with PBS, WT-LYZ (20 μg), or 2-3-7 LYZ variant (20 μg). While the WT-LYZ demonstrated a mean increase in CPU compared to the PBS only treatment, the charge engineered 2-3-7 variant showed a trend toward reduced CPU (p=0.09) (FIG. 7). Additionally, mice were inoculated with $1.6\times10^7$ CFU non-mucoid *Pseudomonas aeruginosa* strain PAO1 prior to treatment with PBS, or increasing doses of 2-3-7 LYZ variant (0.1 μg, 1 μg, 10 μg). Although not statistically significant, the data show a trend towards reduced CPU following treatment with 2-3-7 enzyme (FIG. 8). These studies are ongoing to collect the necessary data points to achieve statistical significance. The following endpoint data will be collected at varied time points after airway exposure as outlined above (12, 24, 36 and 48 hours): mouse survival, bronchoalveolar lavage (BAL) inflammatory cell number, H&E tissue staining of lung scored for severity of inflammation and colony forming units of *P. aeruginosa* in BAL, fluid, lung tissue, blood and spleen. Statistical analysis is performed, with $p\leq0.05$ considered statistically significant.

Example 5: Identification of Further Improved Variants

Based on the early success of this strategy to identify charge engineered lysozyme variants that retain antibiotic activity in the presence of biologically relevant polyanions, it is contemplated that further improved variants are likely to be identified. For example, saturation mutagenesis may be employed at consensus residues identified in the improved lysozyme variants listed here. Systematic mutation by NNS saturation mutagenesis at these residues may yield improved lysozymes variants relative to those disclosed here. Screening libraries thusly generated by using the methodology outlined in Examples 2 and 3 would likely result in isolation of other lysozyme variants exhibiting improved antimicrobial activity under conditions of clinical relevance.

Furthermore, it is contemplated that the antibiotic potential of charge engineered lysozyme variants generated here may be further improved by combination with mutations targeting independent enzyme properties not directly linked to reduction of electrostatic interactions with polyanions. These properties include thermostability, salt sensitivity, pH dependence, substrate specificity, and reduced immunogenicity. These independent properties might be modulated by screening random error-prone gene libraries or by screening computationally designed libraries (Griswold and Bailey-Kellogg, unpublished results).

LIST OF REFERENCES

1. Mizgerd J P (2006) *PLoS Medicine* 3, e76.
2. Mandell L A (2005) *Clinics in Chest Medicine* 26, 57-±.
3. Weber D J, Rutala W, Sickbert-Bennett E E, Samsa G P, Brown V, & Niederman M S (2007) *Infection Control and Hospital Epidemiology* 28, 825-831.
4. Armstrong G L, Conn L A, & Pinner R W (1999) *JAMA* 281, 61-66.
5. Furuya E Y & Lowy F D (2006) *Nat Rev Micro* 4, 36-45.
6. Cole A M, Liao H-I, Stuchlik O, Tilan J, Pohl J, & Ganz T (2002) *J Immunol* 169, 6985-6991.
7. Rogan M P, Geraghty P, Greene C M, O'Neill S J, Taggart C C, & McElvaney N G (2006) *Respiratory Research* 7, 29.
8. Travis S M, Conway B A D, Zabner J, Smith J J, Anderson N N, Singh P K, Greenberg E P, & Welsh M J (1.999) *American Journal of Respiratory Cell and Molecular Biology* 20, 872-879.
9. Nash J A, Ballard T N S, Weaver T E, & Akinbi H T (2006) *J Immunol* 177, 519-526.
10. Akinbi H T, Epaud. R, Bhatt H, & Weaver T E (2000) *J Immunol* 165, 5760-5766.
11. Cole A M, Thapa D R, Gabayan V, Liao H-I, Liu L, & Ganz T (2005) *Journal of Leukocyte Biology* 78, 1081-1085.
12. Dajani R, Zhang Y, Taft P J, Travis S M, Starner T D, Olsen A, Zabner J, Welsh M J, & Engelhardt J F (2005) *Am. J. Respir. Cell Mol. Biol.* 32, 548-552.
13. Hoiby N, Krogh Johansen H, Moser C, Song Z, Ciofu O, & Kharazmi A (2001) *Microbes and Infection* 3, 23-35.
14. Mizgerd J P (2008) *N Engl J Med* 358, 716-727.
15. Ulmer J S, Herzka A, Toy K J, Baker D L, Dodge A H, Sinicropi D, Shak S, & Lazarus R A (1996) *Proceedings of the National Academy of Sciences of the United States of America* 93, 8225-8229.
16. Rogers D F (2007) *Respiratory Care* 52, 1134-1149.
17. Davies J C (2002) (Royal Soc Medicine Press Ltd), pp. 58-67.
18. Ramsey D M & Wozniak D J (2005) *Molecular Microbiology* 56, 309-322.
19. Whitchurch C B, Tolker-Nielsen T, Ragas P C, & Mattick J S (2002) *Science* 295, 1487.
20. Guaqueta C, Sanders L K, Wong C C L, & Luijten E (2006) Biophys. J. 90, 4630-4638.
21. Park W-K, Chung J-W, Kim Y-K, Chung S-C, & Kho H-S (2006) *Archives of Oral Biology* 51, 861-869.
22. van de Weert M, Andersen M B, &. Frokjaer S (2004) *Pharmaceutical Research* 21, 2354-2359.
23. Sanders L K, Xian W, Guaqueta C, Strohman M J, Vrasich C R, Luijten E, & Wong G C L (2007) *Proceedings of the National Academy of Sciences* 104, 15994-15999.
24. Masuda T, Ide N, & Kitabatake N (2005) *Chem. Senses* 30, 667-681.
25. Aizawa T, Koganesawa N, Kamakura Masaki K, Matsuura A, Nagadome H, Terada Y, Kawano K, & Nitta K (1998) *Febs Letters* 422, 175-178.
26. Muraki M, Morikawa M, Jigami Y, & Tanaka H (1989) *European Journal of Biochemistry* 179, 573-579.
27. Kato A, Tanimoto S, Muraki Y, Kobayashi K, & Kumagai I (1992) *Bioscience Biotechnology and Biochemistry* 56, 1424-1428.
28. Muraki M, Morikawa M, Jigami Y, & Tanaka H (1988) *Protein Engineering* 2, 49-54.
29. Bloom J D, Meyer M M, Meinhold P, Otey C R, MacMillan D, & Arnold F H (2005) *Current Opinion in Structural Biology* 15, 447-452.
30. Arnold F H & Georgiou G (2003) *Methods in Molecular Biology* (Humana Press, Totowa).
31. Landau M, Mayrose I, Rosenberg Y, Glaser F, Martz E, Pupko T, & Ben-Tal N (2005) *Nucl. Acids Res.* 33, W299-302.
32. Herman A & Tawfik D S (2007) *Protein Engineering, Design and Selection* 20, 219-226.
33. Markart P, Faust N, Graf T, Na C-L, Weaver T E, & Akinbi H T (2004) *Biochem. J.* 380, 385-392.
34. Satishkurnar R, & Vertegel A (2008) *Biotechnol Bioeng.* 100, 403-412.

What is claimed is:

1. A method of treating a lung infection in a mammalian subject having or at risk of having said infection comprising administering to said mammalian subject a pharmaceutically effective amount of an isolated lysozyme protein having a reduced electrostatic charge relative to the charge of the wild type lysozyme protein, wherein the lysozyme protein is of SEQ ID NO: 1 and the lung infection is due to *Pseudomonas aeruginosa.*

* * * * *